US010821075B1

(12) United States Patent
Blanchard

(10) Patent No.: US 10,821,075 B1
(45) Date of Patent: Nov. 3, 2020

(54) COMPOSITIONS FOR TOPICAL APPLICATION OF A MEDICAMENTS ONTO A MAMMALIAN BODY SURFACE

(71) Applicant: James Blanchard, Tuscon, AZ (US)

(72) Inventor: James Blanchard, Tuscon, AZ (US)

( * ) Notice: Subject to any disclaimer, the term of this patent is extended or adjusted under 35 U.S.C. 154(b) by 0 days.

(21) Appl. No.: 15/648,316

(22) Filed: Jul. 12, 2017

(51) Int. Cl.
*A61K 9/06* (2006.01)
*A61K 9/00* (2006.01)
(Continued)

(52) U.S. Cl.
CPC .............. *A61K 9/06* (2013.01); *A61K 9/0014* (2013.01); *A61K 31/192* (2013.01); *A61K 47/08* (2013.01);
(Continued)

(58) Field of Classification Search
CPC .. A61K 2300/00; A61K 47/08; A61K 9/0014; A61K 47/10; A61K 31/167; A61K 9/122; A61K 47/12; A61K 47/14; A61K 9/0034; A61K 31/245; A61K 47/38; A61K 47/18; A61K 8/046; A61K 9/12; A61K 31/192; A61K 31/573; A61K 47/183; A61K 31/196; A61K 31/375; A61K 31/506; A61K 31/57; A61K 8/25; A61K 9/06; A61K 31/5575; A61K 31/56; A61K 31/565; A61K 31/58; A61K 8/345; A61K 31/135; A61K 31/568; A61K 31/60; A61K 47/20; A61K 47/32; A61K 8/11; A61K 8/42; A61K 2800/652; A61K 31/341; A61K 31/40; A61K 31/405; A61K 31/593; A61K 47/26; A61K 47/36; A61K 8/022; A61K 8/36; A61K 8/4953; A61K 9/0031; A61K 9/0043; A61K 9/0046; A61K 9/0048; A61K 9/0056; A61K 9/501; A61K 31/00; A61K 31/19; A61K 31/522; A61K 8/361; A61K 8/37; A61K 8/375; A61K 8/463; A61K 2800/41; A61K 2800/412; A61K 2800/56; A61K 2800/624; A61K 2800/92; A61K 31/047; A61K 31/137; A61K 31/195; A61K 31/351; A61K 31/355; A61K 31/407; A61K 31/4412; A61K 31/444; A61K 31/5415; A61K 31/616; A61K 38/13; A61K 38/39; A61K 38/4893; A61K 47/02; A61K 47/22; A61K 47/42; A61K 8/0241; A61K 8/19; A61K 8/23; A61K 8/26; A61K 8/60; A61K 8/64; A61K 8/65; A61K 8/735; A61K 9/7023; A61K 9/703; A61K 9/7084; A61K 2800/31; A61K 2800/522; A61K 31/7056; A61K 36/82; A61K 47/24; A61K 8/498; A61K 8/585; A61K 8/67; A61K 8/671; A61K 8/675; A61K 8/676; A61K 8/731; A61K 8/732; A61K 8/8147; A61K 8/86; A61K 8/891; A61K 8/90; A61K 9/107; A61K 9/124; A61K 9/141; A61K 31/44; A61K 9/145; A61K 47/06; A61K 9/0036; A61K 9/4858; A61K 31/225; A61K 31/366; A61K 31/4355; A61K 31/496; A61K 31/501; A61K 31/551; A61K 31/575; A61K 31/65; A61K 47/44; A61K 9/0019; A61K 9/02; A61K 9/1075; A61K 9/14; A61K 9/4825; A61K 9/4866; A61K 38/05; A61K 38/06; A61K 38/04; A61K 8/0208; A61K 8/0212; A61K 31/4172; A61K 38/1741; A61K 39/0011; A61K 39/085; A61K 8/4946; A61K 8/8152; A61K 8/06; A61K 8/068; A61K 8/602; A61K 2800/262; A61K 2800/30; A61K 2800/59; A61K 2800/87; A61K 35/545; A61K 35/74; A61K 38/164; A61K 48/00; A61K 48/005; A61K 8/29; A61K 8/31; A61K 8/44; A61K 8/645; A61K 8/733; A61K 8/892; A61K 8/922; A61K 8/9706; A61K 8/9789; A61K 8/981; A61K 31/20; A61K 31/59; A61K 45/06; A61K 47/34; A61K 31/4709; A61K 31/55; A61K 31/122; A61K 31/216;
(Continued)

(56) References Cited

U.S. PATENT DOCUMENTS

| 4,188,373 A | 2/1980 | Krezanoski ..................... 424/78 |
| 4,393,076 A | 7/1983 | Noda et al. ................... 424/317 |

(Continued)

FOREIGN PATENT DOCUMENTS

| WO | WO9749405 | 12/1997 | ............ A61K 31/52 |
| WO | WO0051575 | 9/2000 | ............... A61K 9/70 |

(Continued)

OTHER PUBLICATIONS

Benzocaine-Topical, Review 2018. See Drug.com.*
(Continued)

*Primary Examiner* — Deborah K Ware
(74) *Attorney, Agent, or Firm* — Hayes Soloway PC

(57) ABSTRACT

Drug-delivery systems are described which can serve as platforms for topical delivery of a variety of active pharmaceutical ingredients (API) to the surface of a mammalian body. Methods for the preparation and use of the compositions are also described. In some embodiments, the disclosed topical formulations include an API, a penetration enhancer/cosolvent, a gelling agent, and a neutralizing agent (to adjust pH). As compared to prior compositions, the disclosed topical formulations use a relatively small number of safe components and are easy to prepare with a high yield of finished product.

16 Claims, No Drawings

(51) Int. Cl.
  *A61K 47/08* (2006.01)
  *A61K 47/32* (2006.01)
  *A61K 47/18* (2017.01)
  *A61K 31/192* (2006.01)

(52) U.S. Cl.
  CPC ............ *A61K 47/18* (2013.01); *A61K 47/183* (2013.01); *A61K 47/32* (2013.01)

(58) Field of Classification Search
  CPC ...... A61K 31/138; A61K 9/10; A61K 31/235; A61K 31/327; A61K 8/34; A61K 8/553; A61K 9/0024; A61K 9/1647; A61K 9/7061; A01N 25/16; A01N 53/00; A01N 59/00; A01N 37/36; A01N 59/06; A01N 2300/00; A01N 59/02; A01N 59/04; A01N 59/08; A01N 25/02; A61Q 19/00; A61Q 7/00; A61Q 5/006; A61Q 17/04; A61Q 19/06; A61Q 1/00; A61Q 19/08; A61Q 19/02; A61Q 19/008; A61Q 19/10; A61Q 5/02; A61Q 5/12; C02F 9/00; C02F 1/001; C02F 1/78; C02F 1/02; C02F 1/72; C02F 1/32; C02F 1/50; C02F 2103/42; Y10S 514/945; Y10S 514/871; A61F 2007/0261; A61F 7/03; A61F 2013/00646; G01N 33/5082; G01N 2570/00; G01N 2800/042; G01N 2800/52; G01N 33/5735; G01N 33/57484; C09K 15/06; A61P 17/02; A61P 13/12; A61P 1/16; A61P 17/00; A61P 17/10; A61P 17/04; A61P 17/06; A61P 29/00; A61P 13/10; A61P 19/02; A61P 19/06; A61P 25/02; C07D 237/20; C07D 237/24; C07D 401/12; C07D 403/12; C07D 405/12; C07D 413/12; C07D 417/12; C07D 473/00; C07D 513/04; A61B 17/54; A61B 2017/00747; A61B 2017/00765; A61M 2037/0007; A61M 35/003; A61M 37/0092; C12N 15/86; C12N 15/8636; C12N 2502/02; C12N 5/00; C12Q 1/6883; C12Q 1/6886; C12Q 2600/106; C12Q 2600/112; C12Q 2600/136; C12Q 2600/158; C12Q 2600/16; Y02A 50/475; Y02A 50/491; Y02A 50/492
  See application file for complete search history.

(56) References Cited

U.S. PATENT DOCUMENTS

| | | | |
|---|---|---|---|
| 4,474,751 A | 10/1984 | Haslam et al. ............... 514/2.4 |
| 4,474,753 A | 10/1984 | Haslam et al. ............... 424/78 |
| 4,478,822 A | 10/1984 | Haslam et al. ............... 424/78 |
| 4,511,563 A | 4/1985 | Schmolka .................... 514/162 |
| 4,534,980 A | 8/1985 | Itoh et al. .................... 514/570 |
| 4,704,406 A | 11/1987 | Stanislaus et al. ........... 514/570 |
| 4,767,619 A | 8/1988 | Murray ........................ 424/78 |
| 4,861,760 A | 8/1989 | Mazuel et al. ................ 514/54 |
| 4,883,660 A | 11/1989 | Blackman et al. ........... 424/78 |
| 4,954,487 A | 9/1990 | Cooper et al. ............... 514/159 |
| 4,999,379 A | 3/1991 | Fankhauser ................. 516/567 |
| 5,032,400 A | 7/1991 | Wiersum et al. .......... 424/195.1 |
| 5,093,133 A | 3/1992 | Wisniewski et al. ......... 424/484 |
| 5,318,780 A | 6/1994 | Viegas et al. ................ 424/427 |
| 5,374,661 A | 12/1994 | Betlach, II ................. 514/772.4 |
| 5,614,171 A | 3/1997 | Clavenna et al. ............. 424/45 |
| 5,618,516 A | 4/1997 | Clavenna et al. ............. 424/45 |
| 5,654,337 A | 8/1997 | Roentsch et al. ............ 514/570 |
| 5,716,609 A | 2/1998 | Jain et al. .................. 424/78.05 |
| 5,837,289 A | 11/1998 | Grasela et al. ............... 424/484 |
| 5,863,560 A | 1/1999 | Osborne ...................... 424/484 |
| 5,897,880 A | 4/1999 | Drizen et al. ................ 424/488 |
| 5,976,566 A | 11/1999 | Samour et al. ............... 424/449 |
| 6,060,085 A | 5/2000 | Osborne ...................... 424/484 |
| 6,083,996 A | 7/2000 | Büyüktimkin et al. ... 514/772.6 |
| 6,277,892 B1 | 8/2001 | Deckner et al. ............ 514/772.4 |
| 6,368,618 B1 | 4/2002 | Jun et al. ..................... 424/449 |
| 6,399,093 B1 | 6/2002 | Petrus ......................... 424/448 |
| 6,420,394 B1 | 7/2002 | Supersaxo .................. 514/338 |
| 6,579,865 B2 | 6/2003 | Mak et al. ................... 514/179 |
| 6,635,674 B1 | 10/2003 | Kaneko et al. .............. 514/562 |
| 6,638,981 B2 | 10/2003 | Williams et al. ............. 514/656 |
| 6,645,520 B2 | 11/2003 | Hsu et al. .................... 424/449 |
| 6,723,345 B2 | 4/2004 | Drizen et al. ................ 424/484 |
| 6,835,392 B2 | 12/2004 | Hsu et al. .................... 424/449 |
| 7,138,394 B2 | 11/2006 | Schwarz et al. ........... 514/226.5 |
| 7,473,432 B2 | 1/2009 | Ceve et al. .................. 424/450 |
| 7,666,914 B2 | 2/2010 | Richlin et al. ............... 514/947 |
| 8,470,886 B2 | 6/2013 | King-Smith et al. ......... 514/570 |
| 8,486,374 B2* | 7/2013 | Tamarkin ............... A61K 9/0014 424/45 |
| 8,541,470 B2 | 9/2013 | Davis .......................... 514/567 |
| 8,795,693 B2* | 8/2014 | Tamarkin ................. A61K 47/26 424/401 |
| 9,012,402 B1 | 4/2015 | Blanchard ............ A61K 31/192 |
| 9,101,662 B2* | 8/2015 | Tamarkin ............... A61K 47/26 |
| 9,180,091 B2* | 11/2015 | Bernick ................. A61K 31/565 |
| 9,289,382 B2* | 3/2016 | Bernick ................. A61K 9/0036 |
| 9,895,359 B1* | 2/2018 | Osborne .................... A61K 9/06 |
| 10,188,661 B2* | 1/2019 | Singer ................... A61K 9/0014 |
| 2001/0012849 A1 | 8/2001 | Wechter ....................... 514/330 |
| 2003/0170295 A1 | 9/2003 | Kim et al. .................... 424/449 |
| 2004/0071767 A1 | 4/2004 | Ceve et al. .................. 424/450 |
| 2005/0042241 A1 | 2/2005 | Cusic et al. .................. 424/401 |
| 2005/0096371 A1 | 5/2005 | Krishnan et al. ............. 514/406 |
| 2005/0158348 A1 | 7/2005 | Schwarz et al. .............. 424/400 |
| 2005/0282755 A1* | 12/2005 | Hart ........................ A61K 38/10 514/2.7 |
| 2006/0241175 A1 | 10/2006 | Schwarz et al. .............. 514/458 |
| 2007/0048360 A1 | 3/2007 | Carrara et al. ................ 424/443 |
| 2007/0141182 A1 | 6/2007 | Niazi ........................... 424/755 |
| 2007/0253911 A1* | 11/2007 | Tamarkin .................. A61K 8/046 424/43 |
| 2008/0069779 A1* | 3/2008 | Tamarkin .................. A61K 8/046 424/45 |
| 2008/0206159 A1* | 8/2008 | Tamarkin .................. A61K 31/56 424/45 |
| 2008/0292560 A1* | 11/2008 | Tamarkin .................. A61K 8/046 424/45 |
| 2008/0299220 A1* | 12/2008 | Tamarkin ............... A61K 9/0014 424/600 |
| 2009/0053290 A1 | 2/2009 | Sand et al. ................... 424/449 |
| 2009/0060990 A1 | 3/2009 | Ceve et al. .................. 424/450 |
| 2009/0062244 A1 | 3/2009 | Schwarz et al. .............. 514/170 |
| 2010/0099767 A1 | 4/2010 | Davis .......................... 514/567 |
| 2011/0021530 A1* | 1/2011 | Billich ...................... A61K 31/00 514/241 |
| 2011/0229536 A1* | 9/2011 | Kvitnitsky ............. A61K 8/0212 424/401 |
| 2013/0052271 A1 | 2/2013 | Sternasty ..................... 424/523 |
| 2015/0017103 A1* | 1/2015 | Tamarkin ................ A61K 47/18 424/45 |
| 2016/0184215 A1* | 6/2016 | Weisenfluh et al. | |
| 2016/0354368 A1* | 12/2016 | Brown ................... A61K 9/7084 |
| 2017/0202852 A1* | 7/2017 | Singer ................... A61K 9/0014 |

FOREIGN PATENT DOCUMENTS

| | | | |
|---|---|---|---|
| WO | WO2005009510 | 2/2005 | |
| WO | WO2007103555 | 9/2007 | ............... A61K 8/49 |
| WO | WO2008049020 | 4/2008 | ............... A61K 9/00 |

(56) References Cited

FOREIGN PATENT DOCUMENTS

| WO | WO2012087749 | 6/2012 | ............ A61F 13/00 |
| WO | WO2015191402 | 12/2015 | ............ A61K 47/10 |

OTHER PUBLICATIONS

Office Action issued in U.S. Appl. No. 15/663,517, dated Jun. 27, 2018 (15 pgs).
Aberle, T. and Burchard, W. (1997), Starches in Semidilute Aqueous Solution. Starch/Stärke, 49: 215-224. doi: 10.1002/star. 19970490602.
Airaksinen, O., Venalainen, J., Piletilainen, T., Ketoprofen 2.5% gel versus placebo gel in the treatment of acute soft tissue injuries. Int. J. Clin. Pharm. Therapy and Tox. 31: 561-563 (1993).
Altman, R.D., Barthel, H.R., Topical therapies for osteoarthritis, Drugs 71:1259-1279 (2011).
American College of Rheumatology Offers Guidance for Assessing Arthritis Pain Medication Usage, Press Release, Amer. Coll. Of Rheumatology, Dec. 22, 2004.
Anon, Carbopol® Ultrez 10 polymer for personal care applications, TDS-225, Lubrizol Advanced Materials, Inc., Cleveland, OH 44141, Jan. 2002.
Anon, Clinical knowledge summary for sprains and strains, National Institute for Health and Care Excellence (NICE), Oct. 2012.
Anon, Easing joint pain: Are NSAIDs right for you? Consumer Reports (2013) http://www.consumerreports.org/health/resources/pdf/best-buy-drugs/2pager_NSAIDs.pdf.
Anon, The pain management market outlook to 2016, Business Insights, 2011). http://www.futuramedical.com/content/products/pain_relief.asp.
Ballerini, R., Casini, A., Chinol, M., Mannucci, C., Giaccai, L., Salvi, M., Study on the absorption of ketoprofen topically administered in man: comparison between tissue and plasma levels, Int. J. Clin. Pharm. Res.VI: 69-72 (1986).
Barkin, R.L., Topical nonsteroidal anti-inflammatory drugs: The importance of drug, delivery, and therapeutic outcome, Amer. J. Ther. Feb. 22, 2012.
Beetge, E., du Plessis, J, Müller, D.G., Goosen, C., van Rensburg, F.J., The influence of the physicochemical characteristics and pharmacokinetic properties of selected NSAID's on their transdermal absorption. Int. J. Pharmaceut. 193: 261-264 (2000).
Bjorkman, D.J., Nonsteroidal Anti-inflammatory Drug-Induced Gastrointestinal Injury. Amer. J. Med. 101(Suppl. 1A): 25S-32S (1996).
Bonina, F.P. and Montenegro, L. Effects of some non-toxic penetration enhancers on in vitro heparin skin permeation from gel vehicles. Int. J. Pharmaceut. 111: 191-196 (1994).
Bystrianyk, R., More hospitalized from NSAID bleeding than all American war casualties, Health Sentinel, 16:00 (Jan. 10, 2010).
Ceschel, et al., Correlation Between the Transdermal Permeation of Ketoprofen an its Solubility in Mixtures of a pH 6.5 Phosphate Buffer and Various Solvents, Drug Delivery, 2002, vol. 9, No. 1, pp. 39-45 (summary only).
Coaccioli, S., Ketoprofen 2.5% gel: a clinical overview, Eur. Rev. Med. Pharmacol. Sci. 15: 943-949 (2011).
Cordero, J.A., Alarcon, L., Escribano, E., Obach, R., Domenech, J., A comparative study of the transdermal penetration of a series of nonsteroidal anti-inflammatory drugs, J. Pharm. Sci. 86: 503-507 (1997).
Cordero, J.A., Camacho, M., Obach, R., Domenech, J., Vila, L., In vitro index of topical anti-inflammatory activity to compare a series of NSAIDs. Eur. J. Pharm. Biopharm. 51: 135-142 (2001).
Desai, D.D., Hasman, D.F., Schmucker-Castner, J.F., Advances in Carbomer polymer technology, BF Goodrich, Specialty Chemicals, Cleveland, OH 44141.
Dreiser, R.L., Topical antirheumatic drug therapy: current practice and future trends. Eur. J. Rheumatol. Inflamm. 14: 3-8 (1994).
European Medicines Agency (EMEA) Press Release http://www.emea.eu.int.
Fabin, B., and Touitou, E., Localization of lipophilic molecules penetrating rat skin in vivo by quantitative autoradiography. Int. J. Pharm. 74: 59-65 (1991).
FDA Issues Public Health Advisory Recommending Limited Use of Cox-2 Inhibitors, FDA Talk Paper, Dec. 23, 2004.
Flouvat, B., Roux, A., Delhotel-Landes, B., Pharmacokinetics of ketoprofen in man after repeated percutaneous administration, Arzneim. Forsch. 39: 812-815 (1989).
Gavura, S., Anti-inflammatory drugs: A closer look at the risks, Science-Based Medicine, Mar. 15, 2013.
Grahame, R. Transdermal non-steroidal anti-inflammatory agents, Brit. J. Clin. Pract. 49: 33-35 (1995).
Gürol, Z., Hekimoğlu, S., Demirdamar, R., Şumnu, M. Percutaneous absorption of ketoprofen. I. In vitro release and percutaneous absorption of ketoprofen from different ointment bases. Pharm. Acta Helv. 71: 205-212 (1996).
Hadgraft, J., du Plessis, J., Goosen, C., The selection of non-steroidal anti-inflammatory agents for dermal delivery. Int. J. Pharmaceut. 207: 31-37 (2000).
Harris, R.H. and Vavra, I., "Ketoprofen", Anti-Inflammatory and Anti-Rheumatic Drugs, vol. II. (Ed., Rainsford, K.D.), CRC Press, Inc., Boca Raton, FL (1985).
Harrison, J.E., Watkinson, A.C., Green, D.M., Hadgraft, J., Brain, K., The relative effect of Azone® and Transcutol® on permeant diffusivity and solubility in human stratum corneum. Pharm. Res. 13: 542-546 (1996).
Knox, R., World's most popular painkiller raises heart attack risk, NPR, Feb. 12, 2013. http://www.npr.org/blogs/health/2013/02/12/171832741/.
Lawrence, R.C., Felson, D.T., Helmick, C.G., Arnold, L.M., Choi, H., Deyo, R.A., Gabriel, S., Hirsch, R., Hochberg, M.C., Hunder, G.G., Jordan, J.M., Katz, J.N., Kremers, H.M. and Wolfe, F., Estimates of the prevalence of arthritis and other rheumatic conditions in the United States. Part II. Arthritis Rheum.58(1):26-35 (2008). doi: 10.1002/art.23176.
Mason, L., Moore, R.A., Derry, S. and McQuay, H.J., Topical NSAIDs for acute pain: a meta-analysis, BMC Family Practice 5:10 (2004). doi:10.1186/1471-2296-5-10; This article can be found online at:http://www.biomedcentral.com/1471-2296/5/10.
Massey, T., Derry, S., Moore, R.A. and McQuay, H.J., Topical NSAIDs for acute pain in adults, Cochrane Database Syst. Rev. Jun. 16, 2010;(6):CD007402. doi: 10.1002/14651858.CD007402.pub2.
McGettigan P, Henry D., Use of non-steroidal anti-inflammatory drugs that elevate cardiovascular risk: an examination of sales and essential medicines lists in low-, middle-, and high-income countries, PLOS Med.10(2):Feb. 12, 2013. e1001388.doi:10.1371/journal.pmed.1001388.
McNeill, S.C., Potts, R.O., Francoeur, M.L. Locally enhanced topical delivery (LETD) of drugs: does it truly exist? Pharm. Res. 9: 1422-1427 (1992).
Meek, I.L., van de Laar, M.A.F.J. and Vonkeman, H.E., Non-steroidal anti-inflammatory drugs: An overview of cardiovascular risks, Pharmaceuticals, 3: 2146-2162 (2010).
Meloun M, Bordovská S, Galla L. The thermodynamic dissociation constants of four non-steroidal anti-inflammatory drugs by the least-squares nonlinear regression of multiwavelength spectrophotometric pH-titration data. J. Pharm. Biomed. Anal. 45: 552-564 (2007).
Merck Announces Voluntary Worldwide Withdrawal of VIOXX®, Merck and Co., Inc., Whitehouse Station, NJ, Sep. 30, 2004.
Moore, R.A., Tramer, M.R., Carroll, D., Wiffen, P.J., McQuay, H.J. Quantitative systematic review of topically applied non-steroidal anti-inflammatory drugs, BMJ 316: 333-338 (1998).
Panchagnula, R. and Ritschel, W.A., Development and evaluation of intracutaneos depot formulation of corticosteroids using Transcutol as a cosolvent: in vitro, ex-vivo and in vivo rat studies. J. Pharm. Pharmacol. 43: 609-614 (1991).
Panchagnula, R., Development of an intracutaneous depot for drugs, Ph.D. Dissertation, University of Cincinnati (1991).
Patel, R.K., Leswell, P.F., Comparison of ketoprofen, piroxicam, and diclofenac gels in the treatment of acute soft-tissue injury in general practice. Clin. Ther. 18: 497-507 (1996).

(56) References Cited

OTHER PUBLICATIONS

Péhourcq, F., Matoga, M., Jarry, C., Bannwarth, B., Study of the lipophilicity of arylpropionic non-steroidal anti-inflammatory drugs. A comparison between LC retention data on a polymer-based column and octanol-water partition coefficients, J. Liq. Chrom. & Rel. Technol. 24: 2177-2186 (2001).
Reddy, K.S., Roy, A., Cardiovascular Risk of NSAIDs: Time to Translate Knowledge into Practice. PLOS Med 10(2): Feb. 12, 2013. e1001389. doi:10.1371/journal.pmed.1001389.
Ritschel, W.A. and Hussain, A.S., In vitro skin penetration of griseofulvin in rat and human skin from an ointment dosage form. Arzneim. Forsch. /Drug Res. 38: 1630-1632 (1988).
Ritschel, W.A. and Hussain, A.S., Influence of selected solvents on penetration of griseofulvin in rat skin, in vitro. Pharm. Ind. 50: 483-486 (1988).
Ritschel, W.A., Panchagnula, R., Stemmer, K., Ashraf, M., Development of an intracutaneous depot for drugs. Skin Pharmacol. 4: 235-245 (1991).
Sarzi-Puttini P, Atzeni F, Lanata L, Bagnasco M., Efficacy of ketoprofen vs. ibuprofen and diclofenac: a systematic review of the literature and meta-analysis, Clin. Exp. Rheumatol., 31(5):731-738 (2013). Epub May 17, 2013.
Shah, V.P., Behl, C.R., Flynn, G.L,, Higuchi, W.I., Schaefer, H., Principles and criteria in the development and optimization of topical therapeutic products. J Pharm Sci. 81: 1051-1054 (1992).
Shah, V.P., Behl, C.R., Flynn, G.L., Higuchi, W.I., Schaefer, H., Principles and criteria in the development and optimization of topical therapeutic products, Int. J. Pharmaceut. 82: 21-28 (1992).
Shah, V.P., Behl, C.R., Flynn, G.L., Higuchi, W.I., Schaefer, H., Principles and criteria in the development and optimization of topical therapeutic products, Pharm. Res. 9: 1107-1111 (1992).
Singh, P., Roberts, M.S., Skin permeability and local tissue concentrations of non-steroidal anti-inflammatory drugs after topical application, J. Pharmacol. Exp. Ther. 268: 144-151 (1994).
Smith, A., Pfizer pulls Bextra off the market, CNN Money, Apr. 7, 2005. http://money.cnn.com/2005/04/07/news/fortune500/bextra/.
Touitou, E., Levi-Schaffer, F., Shaco-Ezra, N., Ben-Yossef, R., Fabin, B., Enhanced permeation of theophylline through the skin and its effect on fibroblast proliferation. Int. J. Pharm. 70: 159-166 (1991).
Vaile, J.H., Davis, P. Topical NSAIDs for musculoskeletal conditions, a review of the literature, Drugs 56: 783-799 (1998).
Wiegand, T.J. and Tarabar, A., Nonsteroidal anti-inflammatory agent toxicity, Medscape, Nov.14, 2012.http://emedicine.medscape.com/article/816117.
W. Xiaomin, W. Longping, Transdermal delivery of nonsteroidal anti-inflammatory drugs mediated by polyamidoamine (PAMAM) dendrimers, J. Pharm. Sci., 96: 595-602 (2007).
Yazdanian, M. and Chen, E., The effect of diethylene glycol monoethyl ether as a vehicle for topical delivery of ivermectin. Vet. Res. Commun. 19: 309-319 (1995).
Office Action issued in corresponding U.S. Appl. No. 14/302,164 dated Sep. 10, 2014 (9 pages).
Office Action issued in corresponding U.S. Appl. No. 14/302,164 dated Nov. 17, 2014 (13 pages).
Notice of Allowance issued in corresponding U.S. Appl. No. 14/302,164 dated Jan. 30, 2017 (8 pages).
"Inactive Ingredient Search for Approved Drug Products, diethylene glycol monoethyl ether" downloaded Jul. 26, 2017 from https://www.accessdata.fda.gov/scripts/cder/iig/getiigWEB.cfm (1 pg).
Allen et al., Ansel's Pharmaceutical Dosage Forms and Drug Delivery Systems, Eighth Edition, Section VI, Liquid Dosage Forms, p. 418, 2005 (2 pgs).
Allen, L.V., "Transdermals: The Skin as Part of a *Drug Delivery System*," International Journal of Pharmaceutical Compounding, vol. 15, No. 4, Jul./Aug. 2011 (8 pgs).
Brown et al., "Dermal and Transdermal Drug Delivery Systems: Current and Future Prospects," Drug Delivery, vol. 13, 2006, pp. 175-187 (13 pgs).
Center for Drug Evaluation and Research (CDER) at the Food and Drug Administration guide, "Naming of Drug Products Containing Salt Drug Substances Guidance for Industry," 2013 and 2015 (10 pgs).
Desai et al., "Advances in Carbomer Polymer Technology," BF Goodrich Specialty Chemicals, 1998 (4 pgs).
Desai et al., "Carbopol® Ultrez™ 10 Polymer; A New Universal Thickener for the Personal Care Industry," BFGoodrich Specialty Chemicals, 1995 (7 pgs).
Elder et al., "Antimicrobial Preservatives Part Two: Choosing a Preservative," American Pharmaceutical Review, Jan. 2012 (12 pgs).
Gattefosse, "Topical Drug Delivery With Lipid Excipients," downloaded on Jul. 27, 2017 from https://www.gattefosse.com/back/files/Topical%20drug%20delivery%20with%20Gattefosse%20lipid%20excipients.pdf (16 pgs).
Lambers et al., "Natural skin surface pH is on average below 5, which is beneficial for its resident flora," International Journal of Cosmetic Science, 2006, 28, pp. 359-370 (2 pgs).
Lubrizol, "Carbopol® Ultrez 10 Polymer for Personal Care Applications (CTFA / INCI Name: Carbomer)," Technical Data Sheet, Jan. 2002 (4 pgs).
Lubrizol, "Neutralizing Carbopol® and Pemulen™* Polymers in Aqueous and Hydroalcoholic Systems," Technical Data Sheet, Sep. 2009 (3 pgs).
Lubrizol, "Not all Carbomers are Created Equally: Ensuring Compliance with Residual Solvent Requirements," LifeScience Polymers, Lubrizol Advanced Materials, Inc., Jul. 2012 (3 pgs).
Moran, Sr. B., "Next-generation Carbopol® Polymer Proves Highly Efficient at Lower pH Levels," Cosmetics & Toiletries, Apr. 2013 (3 pgs).
Ng et al., "Skin Deep: The Basics of Human Skin Structure and Drug Penetration," In: Dragicevic N, Maibach HI (eds) Percutaneous Penetration Enhancers Chemical Methods in Penetration Enhancement: Drug Manipulation Strategies and Vehicle Effects. Springer, Berlin, Heidelberg, 2015, pp. 3-11 (12 pgs).
Notice of Allowance issued in U.S. Appl. No. 14/302,164, dated Feb. 5, 2015 (8 pgs).
Office Action issued in U.S. Appl. No. 14/302,164, dated Nov. 26, 2014 (13 pgs).
Office Action issued in U.S. Appl. No. 14/302,164, dated Sep. 16, 2014 (9 pgs).
Okyar et al., "Novel Formulation Approaches for Dermal and Transdermal Delivery of Non-Steroidal Anti-Inflammatory Drugs," Rheumatoid Arthritis-Treatment, Chapter 2, Jan. 2012 (24 pgs).
Osborne, D.W., "Diethylene glycol monoethyl ether: an emerging solvent in topical dermatology products," Journal of Cosmetic Dermatology, 10, 2011, pp. 324-329 (6 pgs).
Raut et al., "Chemical Penetration Enhancers: For Transdermal Drug Delivery Systems," International Journal of Pharmacy Review & Research, vol. 4, No. 1, 2014, pp. 33-40 (8 pgs).
Roy et al., "Transdermal Delivery of Ketorolac Tromethamine: Permeation Enhancement, Device Design, and Pharmacokinetics in Healthy Humans," Journal of Pharmaceutical Sciences, vol. 84, No. 10, Oct. 1995 (7 pgs).
Schmid-Wendtner et al., "PH and Skin Care," ABW Wissenschaftsveriag, table of contents, 2007 (3 pgs).
Schmid-Wendtner et al., "The pH of the Skin Surface and Its Impact on the Barrier Function," Skin Pharmacology and Physiology, 2006, 19, pp. 296-302 (8 pgs).
Stanos, S. P., "Topical Agents for the Management iof Musculoskeletal Pain," Journal of Pain and Symptom Management, vol. 33, No. 3, Mar. 2007 (14 pgs).
Vaidyanathan et al., "Effect of pH and solubility on in vitro skin penetration of methotrexate from a 50% v/v propylene glycol-water vehicle," International Journal of Pharmaceutics, 25 (1985), pp. 85-93 (9 pgs).
Vikas et al., "Penetration Enhancers: A Novel Strategy for Enhancing Transdermal Drug Delivery," International Research Journal of Pharmacy, 2(12), 2011 (6 pgs).
Wiechers, J.W., "Formulation at pH 4-5: How Lower pH Benefits the Skin and Formulations," Cosmetics & Toiletries, Jul. 2013, (8 pgs).

(56) References Cited

OTHER PUBLICATIONS

Woodall et al., "Effect of formulation pH on transdermal penetration of antiemetics formulated in poloxamer lecithin organogel," Int J Pharm Compd, 2013, 17(3), pp. 247-253, abstract (1 pg).

Zlotogorski, A., "Distribution of skin surface pH on the forehead and check of adults," Arch Dermotol Res, 1987, 279, pp. 398-401 (4 pgs).

International Search Report and Written Opinion issued in application No. PCT/US 18/41692, dated Oct. 2, 2018 (9 pgs).

Wikipedia, "Dental anesthesia", Sep. 2016, retrieved on Sep. 12, 2018 from https://en.wikipedia.org/w/index.php title=Dental_anesthesia&oldid=737595189 (3 pgs).

First Office Action issued in corresponding Chinese Patent Appln. Serial No. 201580042862.3, dated Mar. 5, 2019, with English translation, 12 pgs.

Osborne et al. "Skin Penetration and Permeation Properties of Transcutol®—Neat or Diluted Mixtures," AAPS PharmSciTech, vol. 19, No. 8, Nov. 2018 (22 pgs).

Patel et al., "Emulgel: A Novel Approach for Topical Drug Delivery System," ejbps, 2016, vol. 3, Issue 9, 501-506 (6 pgs).

Schmid et al., "The Concept of the Acid Mantle of the Skin: Its Relevance for the Choice of Skin Cleansers," Dermatology 1995;191:276-280 (5 pgs).

Swarbrick et al., "Drug Permeation through Human Skin: I. Effect of Storage Conditions of Skin," The Journal of Investigative Dermatology, 78:63-66, 1982 (4 pgs)

Chinese Office Action (w/translation) issued in application No. 201580042862.3, dated Sep. 20, 2019 (12 pgs).

\* cited by examiner

COMPOSITIONS FOR TOPICAL APPLICATION OF A MEDICAMENTS ONTO A MAMMALIAN BODY SURFACE

FIELD OF THE INVENTION

The subject disclosure relates to compositions and methods for the topical administration of active pharmaceutical ingredients (API) to treat a variety of therapeutic indications.

BACKGROUND

Many topical delivery systems suffer from one or more shortcomings that can limit their utility, including: (a) an unnecessarily large number of ingredients, some of which are present in trace amounts and contribute little, if anything, to the overall performance of the delivery system, (b) the use of ingredients which can cause skin sensitization reactions—an issue that limits the amount of these preparations that can be applied to the skin and the length of time for which they can be applied, (c) the very common use of volatile ingredients, e.g., ethanol and/or isopropanol, which can evaporate and destabilize the formulation and render it unsightly and/or ineffective, (d) the use of ingredients with poor sensory characteristics, e.g., greasy and/or smelly, which can lead to poor patient compliance, (e) the use of ingredients that can stain clothing, and (f) the use of overly-complicated formulations which can be time-consuming to prepare, difficult to scale-up for manufacturing purposes, and can result in low yields of finished product.

Table I illustrates a number of commercially available topical delivery systems for nonsteroidal anti-inflammatory drugs (NSAIDs).

TABLE I

Commercially Available Topical NSAID Products

| PRODUCT | MANUFACTURER | ACTIVE (% w/w) | EXCIPIENTS |
| --- | --- | --- | --- |
| Voltarol 1.16% Emulgel Gel | Novartis | Diclofenac Diethylammonium (1.16) | Isopropyl Alcohol, Cocoyl caprylocaprate, Carbopol 980, Diethylamine, Fragrance (Perfume Cream 45), Mineral Oil (Liquid Paraffin Heavy), Propylene Glycol, Macrogol or (Polyoxyl 20) Cetostearyl ether, Purified water |
| Voltarel 12 Hour Emulgel P | Novartis | Diclofenac Diethylammonium (2.32) | Propylene glycol (50 mg/g gel), Butylhydroxytoluene (0.2 mg/g gel), carbomers, Cocoyl caprylocaprate, Diethylamine, Isopropyl alcohol, Liquid Paraffin, Macrogol Cetostearyl ether, Oleyl alcohol, Perfume eucalyptus sting, Purified water |
| Feldene 5 mg/g Gel | Pfizer Ltd. | Piroxicam (0.5) | Benzyl alcohol, carbopol 980, di-isopropanolamine, ethyl alcohol, hydroxyethyl cellulose, propylene glycol, Purified water |
| Oruvail 2.5% Gel | Sanofi | Ketoprofen (2.5) | Carbopol, Triethanolamine, Lavender Oil, Ethanol, Purified Water |
| Powergel 2.5% Gel | Menarini | Ketoprofen (2.5) | Carbomer 940, Ethanol, Neroli Essence, Lavender Essence, Trolamine, Purified Water |
| Ketoprofen 2.5% w/w Gel | Pinewood Health Care | Ketoprofen (2.5) | Carbomer, Triethanolamine, Lavender essential oil, Ethanol (95%), Purified Water |
| Traxam 3% w/w Gel | Amdiphann Mercury Co. | Felbinac (3) | Carbomer, Diisopropanolamine, Ethanol (96%), Purified Water |
| Boot's Ibuprofen Gel | The Boots Co., PLC | Ibuprofen (5) | Ethylhydroxycellulose, Sodium Hydroxide, Benzyl alcohol, Isopropyl alcohol, Purified Water |
| Fastum 2.5% w/w Gel | Menarini | Ketoprofen (2.5) | Carbomer 940, Ethanol, Neroli Essence, Lavender Essence, Trolamine, Purified Water (may also contain methyl & propyl paraben & diethanolamine) |
| Gabrilen Gel | Kreussler | Ketoprofen (2.5) | Carbomer, ethanol (96%), isopropanol, ammonia solution (10%), Purified water |
| Effeckton Gel | Teofarma SRL | Ketoprofen (2.5) | Carbomer 940, ethanol (96%), isopropanol, Conc. Ammonia solution, Purified water |
| Togal Mobil Gel | Togal-WERK AG | Ketoprofen (2.5) | Carbomer, ethanol (96%), isopropanol, ammonia solution (10%), Purified water |

All of these commercial NSAID product formulations suffer from one or more of the shortcomings mentioned above. For example, of the 12 products listed, 6 utilize isopropanol, 9 use ethanol, and 3 use both ethanol and isopropanol. In addition, of the 11 products that use a carbomer as the gelling agent, only 5 identify the carbomer used, and of these, 3 of the 5 products use Carbopol 940. Carbopol 940 was one of the earlier carbomers developed and used benzene (a known carcinogen) as a polymerization solvent during the manufacturing process. Other Carbopols which utilized benzene include Carbopol 941, Carbopol 934, Carbopol 934P, and Carbopol 1342. Their use is no longer advocated and other benzene-free Carbopol or Pemulen polymers are now recommended as substitutes (Anon, Not all polymers are created equally: Ensuring compliance with residual solvent requirements, PH-011 (Revision Date: Jul. 3, 2012) Life Science Polymers, Lubrizol Advanced Materials, Inc., Cleveland, Ohio 44141).

SUMMARY

Topical delivery systems for active pharmaceutical ingredients (API) are disclosed herein. As explained below in detail, the teachings of the present disclosure overcome numerous shortcomings of current commercially-available topical formulations. The subject disclosure provides guidelines and platforms for the efficacious delivery of various medicaments (API) where topical delivery is a viable route of administration. The present disclosure also provides detailed methods for the preparation of exemplary embodiments of the described topical delivery platforms.

The disclosed topical formulations include various ingredients, such as at least one API, one or more skin penetration enhancers, at least one gelling agent, and a solvent (also referred to as a carrier, vehicle, or cosolvent). In some embodiments, the disclosed topical formulations also include a neutralizing agent to adjust pH, a chelating agent, a preservative, a fragrance, and optionally, a coloring agent.

The disclosed topical delivery systems can be used with any appropriate API, including but not limited to NSAIDs. In some embodiments, the API used in the formulations disclosed herein is ketoprofen. Similar results to ketoprofen may, in some cases, be directly extrapolatable to other API, and the drug-delivery platforms described herein will be adaptable to many additional API with only minor modifications. In some cases, the disclosed drug-delivery platforms are devoid of any volatile constituents (e.g., lower alcohols such as ethanol and isopropanol), thereby minimizing the possibility of evaporation in the container or upon application to the skin, as well as reducing the possibility of skin irritation. The gel compositions described herein are capable of maintaining excellent physical stability when stored in containers (i.e., jars) for over eight years. In addition, accelerated stability studies indicate that the API ketoprofen is sufficiently stable chemically to afford at least a two-year shelf life. The disclosed example formulations can be used to treat a variety of musculoskeletal conditions by providing excellent relief of pain without systemic side effects or cutaneous irritation. This has been demonstrated by the use of these exemplary ketoprofen formulations by more than two dozen subjects over a 12-year period.

In summary, in one aspect of the disclosure there are provided compositions for topical application onto the mammalian body surface, the compositions comprising: at least one active pharmaceutical ingredient (API); a penetration enhancer; a gelling agent; and an aqueous carrier.

In a preferred aspect the at least one API is selected from the following types of topical agents: anorectal preparations, antiseptics, germicides, dermatological agents, oral cavity preparations, nail preparations, nasal preparations, ophthalmic preparations, otic preparations, and vaginal preparations. Preferably the API comprises a pharmaceutically acceptable ester, amide, prodrug, salt form, solvate, or in the case of a chiral molecule, a racemate or enantiopure compound.

In another aspect the penetration enhancer is selected from the group consisting of: alcohols, amides, esters, fatty acids, glycols, pyrrolidones, sulfoxides, surfactants, terpenes, urea, cyclodextrins, water, vitamin E, and phospholipids. Preferably the penetration enhancer comprises diethylene glycol monoethyl ether (DEGEE), more preferably Transcutol®P.

In another aspect the gelling agent is selected from the group consisting of: an inorganic gelling agent, an organic gelling agent, a hydrogel, and an organogel. Preferably the gelling agent comprises a carbomer polymer.

In a particularly preferred aspect, the API is present in a weight percent of between 0.01 and 50, the penetration enhancer is present in a weight percent of between 0.10 and 49.9, and the gelling agent is present in a weight percent of between 0.15 and 5.0. In such aspect the penetration enhancer preferably is present in a weight percent of between 3 and 30. Also preferably present is at least one of a preservative, a chelating agent, a neutralizing agent, a fragrance, and optionally, a coloring agent. In such embodiment the preservative preferably is selected from the group consisting of: ascorbyl palmitate, benzalkonium chloride, benzethonium chloride, benzyl alcohol, Bronopol, butylated hydroxyanisole (BHA), butylated hydroxytoluene (BHT), caprylyl glycol, cetrimide, chlorhexidine, chlorphenesin, dehydroacetic acid, DMDM Hydantoin, ethylhexylglycerin, Euxyl K500, Euxyl K940, Euxyl PE 9010, Germaben II, Germall Plus, glyceryl caprylate, imidazolidinyl urea, kojic acid, methylchloroisothiazolinone, methylisothiazolinone, methyl-, ethyl-, propyl-, and butyl-paraben, Optiphen DP, Optiphen DLP, Paragon II, Paragon III, Paragon MEPB, Paragon PPM, pentylene glycol, 2-phenoxyethanol, potassium sorbate, propyl gallate, sodium benzoate, sodium metabisulfite, α-tocopherol, and tocopheryl acetate. The chelating agent preferably comprises disodium ethylenediaminetetraacetic acid (EDTA) dihydrate, and the neutralizing agent preferably is selected from the group consisting of: sodium hydroxide, potassium hydroxide, ammonium hydroxide, L-Argininc, aminomethyl propanol, triethanolamine, tromethamine, tetrahydroxypropylethylenediamine, PEG-15 Cocamine, diisopropanolamine, or triisopropanolamine.

In another preferred embodiment the API is a nonsteroidal anti-inflammatory drug (NSAID) present in a weight percent between 0.1 and 25.0, the penetration enhancer is DEGEE, present in a weight percent between 3.0 and 30, and the gelling agent is a carbomer polymer present in a weight percent between 0.3 and 3.5, and further optionally comprises a neutralizing agent, a chelating agent, a preservative, and a fragrance, wherein the neutralizing agent preferably is present in a weight percent of between 0.2 and 2.5, the chelating agent is present in a weight percent of between 0.04 and 0.10, the preservative is present in a weight percent of between 0.01 and 1.5, the fragrance is present in a weight percent of between 0.1 and 0.8, the neutralizing agent preferably comprises triethanolamine and the chelating agent comprises disodium EDTA dihydrate. In such preferred embodiment, the composition has a pH between 4.0 and 9.0, preferably a pH between 4.4 and 5.0.

In yet another embodiment the composition comprises a smooth muscle relaxant, preferably a smooth muscle relaxant selected from the group consisting of: carisoprodol, chlorzoxazone, cyclobenzaprine, baclofen, dantrolene, metaxolone, methocarbamol, orphenadrine, and tizanidine, and/or an agent which can increase the blood flow to the site of administration, preferably adenosine, alprostadil, amlodipine, capsaicin, diltiazem, dipyridamole, felodipine, hydralazine, isosorbide mononitrate, menthol, methyl salicylate, minoxidil, mustard oil, nicorandil, nimodipine, tartrazine, and verapamil.

In still yet another aspect, the API is selected from the group consisting of: *Aloe vera*, *Arnica Montana*, *Boswellia serrata*, bromelain, *Calendula officinalis*, *Colchicum autumnale*, Evening Primrose Oil, *Zingiber officinalis* (ginger), *Ledum palustre* (marsh-tea), quercetin, *Rhus toxicodendron* (poison ivy), rutin, *Symphytum officinale* (comfrey), Tea Tree Oil, and *Curcuma longa* (turmeric).

Other advantages and features of the methods and formulations disclosed herein will become apparent from the following detailed description. However, it should be understood that the detailed description and the specific examples provided, while indicating some embodiments are provided by way of illustration only and various modifications also fall within the scope and spirit of the present disclosure.

Definitions

Unless otherwise indicated, the definitions and terminology used herein are intended to be applicable to all aspects of the disclosure and are not intended to be limiting in any way.

The terms "a", "an", and "the" as used herein are intended to include both the "singular" and "plural" forms, unless the context clearly indicates otherwise.

The term "active pharmaceutical ingredient (API)" as used herein refers to an ingredient in a pharmaceutical product that is biologically active. The term "API" should be considered synonymous with the terms "drug" or "medicament". It should also be noted that the term "API" can be used to denote both the singular and plural forms of the term, as will be obvious from the context where used.

The term "agent" as used herein includes a compound or mixture of compounds that, when added to a composition, produces a particular effect on the properties of the composition. For example, a composition containing a thickening agent will be more viscous than a comparable composition that lacks the thickening agent. It should be understood that the word "agents" referred to can also include their pharmaceutically acceptable esters, amides, prodrugs, salt forms, and solvates, and in the case of chiral molecules, their racemates or enantiopure compounds.

The term "chirality" refers to a geometric property of some molecules and ions. A chiral atom (or chiral center) is usually a carbon atom that has 4 different substituents attached to it. Molecules possessing chiral atoms (usually only one) can exist as two stereoisomers known as enantiomers. Stereoisomers are isomeric molecules that have the same molecular formula and sequence of bonded atoms, but that differ only in the three-dimensional orientation of their atoms in space. Two stereoisomers that are non-superimposable mirror images of each other are referred to as enantiomers. The chiral center in one has the opposite configuration in the other. Enantiomers of each other have the same physical properties, except for the direction in which they rotate polarized light. Enantiomers are given the designation R (+) or S (−), depending on the direction in which they rotate polarized light. Enantiopure compounds refer to samples having, within the limits of detection, molecules of only one chirality, i.e., pure R (+) or pure S (−). A "racemate" or "racemic mixture" is one that has equal amounts of left-(S) and right-(R) handed enantiomers of a chiral molecule. A racemate is optically inactive, meaning that there is no net rotation of plane-polarized light. Although the two enantiomers rotate plane-polarized light in opposite directions, the rotations cancel out because they are present in equal amounts in a racemic mixture.

The term "cosolvent" as used herein refers to water-miscible organic solvents used in a formulation to increase the aqueous solubility of substances or to enhance the chemical stability of a drug. As used herein, the term should be considered synonymous with "solvent".

The term "first-pass effect" as used herein, sometimes also referred to as "first-pass metabolism" or "pre-systemic metabolism", refers to the intestinal and/or hepatic degradation or alteration of a drug or substance taken by mouth, after absorption, removing some of the active substance from the blood before it enters the general circulation.

The terms "formulation", "drug-delivery system", "composition", and "platform" as used herein are meant to be equivalent terms referring to a composition of matter for pharmaceutical use. In more specific language, these terms are also synonymous with the term "dosage form" which is defined as a combination of drug substances and excipients (inactive ingredients) designed to facilitate dosing, administration, and delivery of medication to the patient.

The term "gel" as used herein is defined as a semisolid formulation which consists of an external solvent phase, is hydrophobic or hydrophilic in nature, and is immobilized within the available spaces of a three-dimensional network.

The term "intracutaneous depot" as used herein refers to a region of the epidermis, i.e., the stratum corneum and the viable epidermis, where drug accumulates and forms a reservoir (depot) of drug.

The term "penetration enhancer" as used herein includes an agent or combination of agents that facilitates the transport of molecules, e.g., API, through the major skin barrier, the stratum corneum.

The term "pharmaceutically acceptable" means compatible with the treatment of the mammalian body, i.e., humans and/or animals.

The term "pharmaceutically acceptable salt" as used herein refers to an ionizable drug molecule, e.g., an acid (negative ion) that has been combined with a counter-ion (positive) to form a neutral complex. When these salts are administered they dissociate (ionize) into their parent moiety and the positive counter-ion (e.g., $Na^+$, $K^+$, etc.) in the case of acidic drugs or their parent moiety and the corresponding negative counter-ion (e.g., $Cl^-$, $Br^-$, etc.) in the case of bases. Thus, the species providing the therapeutic effect in vivo is the parent (active) moiety, e.g., the therapeutic effect of ketoprofen sodium is due to the "active moiety", i.e., ketoprofen, not sodium. The United States Pharmacopeia (USP) acknowledged this concept in their recent "Salt Policy" (Anon, Monograph Naming Policy for Salt Drug Substances in Drug Products and Compounded Preparations, published in USP General Chapter <1121> Nomenclature, effective May 1, 2013), which states that the USP will use the name of the active moiety, instead of the salt, for all new drug product monographs containing an active ingredient that is a salt.

The term "pH" as used herein should be considered an "apparent pH" to acknowledge the fact that the behavior of a pH electrode in a complex multicomponent dermatological vehicle which is not totally aqueous in nature cannot be considered a "pH" in the strictest sense.

The term "pH adjusting agent" or "neutralizing agent" as used herein refers to a compound added to a composition in order to change the pH of the composition. Examples of such agents include pharmaceutically acceptable acids, bases, and buffers.

The term "phytomedicines" (also called "botanicals") as used herein refers to herbal medicines prepared from plant materials or plant-derived natural substances used to treat ailments or alleviate symptoms thereof.

The term "rheology" as used herein refers to the study of the flow properties of matter. Two of the most relevant terms in the field of rheology are "viscosity", which is defined as the resistance to flow, and "yield value", which quantifies initial resistance to flow under stress; hence, it is also referred to as "yield stress".

The term "rheology modifier" as used herein refers to agents that alter the flow properties of a formulation. Rheology modifiers can be sub-classified into two categories, (a) Thickening agents and (b) Gelling agents. A thickening agent is a compound that increases the viscosity of a composition without substantially changing its other properties. A thickening agent may be a pure substance or a mixture of different substances. The term "gelling agent" (or "gellant") as used herein means one or more ingredients that will turn a water or oil phase into a gel, which is thickened, but typically without stiffness. Emulsions thickened with gelling agents will generally be more mobile and fluid rather than stiff. In essence, all gels are thickening agents, but not all thickening agents are gels.

The term "solvation" as used herein refers to the attraction and association of molecules of a solvent with molecules or ions of a solute. Solvation of a solute by water is called "hydration". Many organic molecules, as well as inorganic molecules, form crystals that incorporate water into their crystalline structure without chemical alteration of the organic molecule. Such hydrates are said to contain "water of crystallization" or "water of hydration".

The term "syneresis" as used herein refers to the contraction of a gel accompanied by the exudation of liquid.

The terms "Thixotropy" and "Thixotropic" refer to a property exhibited by certain gels of becoming fluid when shaken or agitated and returning to a more viscous semisolid state upon standing.

As used herein, the term "topical" refers to a semisolid preparation (e.g., ointment, cream, or gel) to be applied onto a mammalian body surface to provide a desired therapeutic effect (e.g., pain relief) locally at or beneath the application site.

"Topical delivery" as used herein refers to the application of a drug-containing formulation to an accessible body surface, e.g., the skin, nail(s), and various mucosae, including buccal, nasal, ocular, otic, rectal, and vaginal. When a formulation is applied to the skin the goal is to confine the pharmacological effect of the drug to the surface of the skin or within the epidermal region of the skin directly beneath the application site in order to obtain a pharmacological effect within musculature, vasculature, joints, etc. This latter effect is sometimes referred to as "regional delivery" and requires percutaneous absorption and deposition.

"Topical formulation" as used herein denotes a composition that is suitable for topical delivery to a mammalian body, i.e., human and/or animal. A topical formulation is designed to produce a local effect at or beneath the application site.

The terms "treating" or "treatment" as used herein refer to procedures for achieving a desired outcome.

The previous definitions have been provided for clarity and should be interpreted as having a meaning that is consistent with their meaning in the context of the relevant art and the present disclosure and should not be interpreted in an idealized or overly formal sense unless expressly so defined herein.

In the following description, numerous specific details will be taught in order to provide a thorough understanding of the disclosed subject matter. However the presently disclosed subject matter may be practiced without these specific details, in some cases. Indeed, various modifications may be made without departing from the spirit and scope of the disclosure. The present disclosure is therefore not intended to be strictly limited to the specific example embodiments discussed in the following description.

DETAILED DESCRIPTION

Topical delivery is a viable and often a preferred mode of administration for medicaments in some circumstances (Allen, L. V., Transdermals: The Skin as Part of a Drug Delivery System, Int. J. Pharm. Compounding 15: 308-315 (2011); Brown, M. R., Martin, G. P., Jones, S. A., Akomeah, F. K., Dermal and Transdermal Drug Delivery Systems: Current and Future Prospects, Drug Delivery 13: 175-187 (2006); Stanos, S. P., Topical Agents for the Management of Musculoskeletal Pain, J. Pain Symptom Management 33: 342-355 (2007)). including but not limited to the following: (1) when the patient is unconscious or vomiting, or merely unable to swallow an oral dosage form, (2) when it may be advantageous to avoid the gastrointestinal (GI) tract due to absorption difficulties caused by GI pH, enzymatic activities, or drug interactions with food, drink or other orally administered drugs, (3) when it is desirable to avoid the first-pass effect, thereby avoiding possible deactivation of the drug by digestive and/or liver enzymes, (4) when a non-invasive alternative is desired to avoid the inconvenience and pain of parenteral therapy, (5) when topical administration provides extended therapy with a single application which may, in turn, improve patient compliance over other regimens requiring more frequent dosing and, in turn, reduce overall health treatment costs, (6) when it is desirous to extend the activity of drugs with a short half-life by means of a prolonged release of drug from a reservoir of drug in the topical delivery system, (7) when it may be desirous to rapidly terminate the drug effect by removal of the dosage form from the body surface, and (8) when a localized effect of the drug is desired at or beneath the site of application, and where significant systemic absorption is to be avoided to minimize toxicity, e.g., the use of NSAIDs to treat musculoskeletal pain. These examples illustrate that there is a significant role for the topical route in the delivery of medicaments and, as a result, the principles and procedures described herein can provide useful techniques for formulating efficacious topical delivery systems.

Formulations for topical delivery of one or more active pharmaceutical ingredients (API) are provided herein. Applying an API to the skin can result in three possible outcomes: (1) the drug can be delivered ONTO the skin's surface, which is appropriate in cases such as treating skin diseases, sunscreens, cosmetics, anti-infectives, and insect repellants, for example; (2) the drug can be delivered INTO the skin for localized dermatologic effects, or for deeper penetration (percutaneous absorption), e.g., to treat muscular aches and pains; or (3) the API can be transported THROUGH the skin—a process known as "transdermal" delivery. Transdermal formulations are designed to deliver drugs THROUGH the skin to achieve systemic effects that may occur distant from the site of application.

For a "topical" formulation, an optimal outcome is that retention of the API ON or IN the skin will be maximized with little or no drug flux THROUGH the skin. For clarity, the term "penetration" is used herein to describe entry of an API INTO the upper epidermal layers of the skin, while the term "permeation" is used herein to describe API transport THROUGH the skin and into the systemic circulation.

In some embodiments, the disclosed compositions and formulations for topical application include one or more API and one or more penetration enhancers to promote penetration of the API into the upper epidermal layers of the skin. In many example embodiments, the disclosed compositions and formulations are delivered using an aqueous vehicle or carrier. Some particular embodiments of the disclosed compositions and formulations also include at least one gelling agent, and optionally include one or more of the following: a preservative, a neutralizing agent, a chelating agent, a fragrance, and a coloring agent. Numerous example embodiments are described in detail below and many variations may be made based on the teachings provided herein.

The topical delivery systems described herein may utilize any suitable vehicle or carrier for the API. The design of the vehicle chosen for topical delivery of an API is an important factor in determining the efficacy of the final product (Barkin, R. L., Topical nonsteroidal anti-inflammatory drugs: The importance of drug, delivery, and therapeutic outcome, Amer. J. Ther. 22: 388-407 (2015)). In addition to providing a stable medium for the active ingredient to ensure a suitable shelf life for the product, the vehicle should also possess a number of other attributes. For example, the vehicle should enable the drug to be released rapidly onto the surface of the skin and, if desired, should promote rapid penetration of the drug through the skin into the subcutaneous tissues. Furthermore, the vehicle itself should possess good physical stability, with only minimal evaporation of any components (e.g., cosolvents) as excessive evaporation can lead to precipitation of the drug as an insoluble and unsightly film on the surface of the skin. If such a precipitate should form, as happens with some formulations, little or no absorption of the drug can occur.

As illustrated by the examples in Table I, many topical NSAID products currently available use either ethanol and/or isopropanol to help incorporate a water-insoluble drug into an aqueous vehicle. The presently disclosed formulations do not require volatile cosolvents and thus avoid evaporation and resultant drug precipitation issues. In accordance with embodiments of the subject disclosure, the vehicle may provide a pleasant sensory experience (feel and fragrance) to help ensure patient compliance. Other desirable attributes of the vehicle include a rapid blending into the skin following application, a non-staining of clothing, and ease of removal when washing with water.

The disclosed compositions and formulations may use any appropriate vehicle. In some embodiments, the vehicles possess all of the attributes discussed above and are easy to prepare. In addition, in some embodiments, the vehicle may use a small number of ingredients that all have a good safety profile (the various Ingredients used in monographs in: "Cosmetic Ingredients Review" may be found on the label of a personal care product and searched using online data-bases. Ingredients are often referred to on the label of a personal care product by the ingredient name as it appears in the International Nomenclature of Cosmetic Ingredients (INCI), known as the INCI Name. CIR reviews ingredients, not products. Furthermore, as a matter of practice, CIR does not usually review fragrances, colors, or flavorings; Inactive Ingredient Search for Approved Drug Products can be found using an online database search provided by the U.S. Food and Drug Administration.), which can minimize development and manufacturing costs as well as accelerate regulatory approval.

The disclosed novel topical delivery systems incorporate a penetration enhancer, in some embodiments, to assist in transporting the API across the stratum corneum (SC) barrier. It is well established that the diffusional resistance to the penetration of an API into the skin resides in the SC. This resistance is believed to be due to a complex interaction between lipid and proteinaceous components which creates distinct hydrophilic and lipophilic penetration pathways. Most drugs do not have the inherent ability to penetrate the SC to a sufficient degree and require substantial enhancer augmentation due to generally poor intrinsic diffusivity. A number of penetration-enhancing approaches have been investigated and one of the most popular approaches to date has been the use of "chemical" penetration enhancers.

A listing of several chemical penetration enhancers is shown in Table II (Raut, S. V., Nemade, L. S., Desai, M. T., Bonde, S. D., Dongare, S. U., Chemical penetration enhancers: for transdermal drug delivery systems, Int. J. Pharm. Rev. Res. 4: 33-40 (2014)). The examples shown for each chemical class are intended to be representative rather than exhaustive.

TABLE II

Examples of Chemical Penetration Enhancers

| Chemical Classification | Enhancer Type (with Examples) |
|---|---|
| Alcohols | Short-chain (e.g., ethanol, isopropanol) Long-chain (e.g., decanol, hexanol, octanol, myristyl alcohol |
| Amides | Azone |
| Esters | Ethyl acetate, oleyl acetate, isopropyl myristate, propylene glycol monocaprylate, octyl salicylate |
| Fatty acids | Laurie acid, linoleic acid, oleic acid, palmitic acid, isostearic acid |
| Glycols | Propylene glycol, dipropylene glycol, ethoxydiglycol |
| Pyrrolidone | N-methyl-2-pyrrolidone, 2-pyrrolidone |
| Sulfoxides | Dimethyl sulfoxide, decylmethyl sulfoxide |
| Surfactants | Anionic surfactants (e.g., sodium lauryl sulfate), Cationic surfactants (e.g., alkylpyridinium halide, alkyl dimethylbenzylammonium halides), Non-ionic surfactants (e.g., Span 80, Tween 80) |
| Terpenes | Cineol, eugenol, D-limonene, linalool, menthol, menthone |
| Urea | Carbarnide |
| Miscellaneous | Cyclodextrins, water, vitamin E, phospholipids |

Although the classification in Table 11 is based on chemical structure, it is important to note that chemicals belonging to the same group may exert their effect on the skin via different mechanisms. An ideal skin penetration enhancer should have the following properties (Vikas, S., Seema, S., Gurpreet, S., Rana, A. C., Baibhav, J., Penetration enhancers: a novel strategy for enhancing transdermal drug delivery, Int. Res. J. Pharmacy 2(12): 32-36 (2011)): (1) non-toxic, non-irritating and non-allergenic; (2) work rapidly, and the activity and duration of effect should be both predictable and reproducible; (3) no pharmacological effect within the body; (4) work unidirectionally, i.e., the enhancer should allow therapeutic agents into the body while preventing the loss of endogenous materials from the body; (5) compatible with the drugs and excipients in the formulation; and (6) cosmetically acceptable with an appropriate skin "feel".

An effective penetration enhancer should be capable of exerting two effects. First, it must enable the API to be released from the formulation matrix employed, and second, it must alter the SC barrier sufficiently to enhance the diffusion of the API into the skin. Despite much research to date, no single penetration enhancer with these desired properties has been identified, and in some investigations, it has been observed that a combination of enhancers may be necessary in order to achieve the duality of effects needed. The formulations disclosed herein may include a single penetration enhancer, in some embodiments, while in other embodiments, more than one penetration enhancer may be used.

In some embodiments, the novel compositions described herein include a gel matrix into which a penetration enhancer is incorporated. As noted earlier, gels are semisolid systems consisting of dispersions made up of either small inorganic particles or large organic molecules enclosing and interpenetrated by a liquid. Gels can be clear when all of the particles completely dissolve in the dispersing medium or gels may be translucent or opaque when some particles remain undissolved. Due to their relative ease of preparation and excellent sensory properties, gels are well-suited for topical administration.

Gels are typically prepared with substances known as gelling agents (or gellants), which undergo a high degree of cross-linking or association when hydrated and dispersed or dissolved in the dispersing medium. This cross-linking or association of the dispersed phase will alter the viscosity of the dispersing medium. The movement of the dispersing medium is restricted by the dispersed phase, and the viscosity of the system is increased. Gels that do not appear to have discrete particles are called one-phase systems. Gels that include small discrete particles are referred to as two-phase systems. Two-phase systems are thixotropic and when the particle size is large, they are referred to as magmas.

Gels are categorized using two classification systems. One divides gels into organic and inorganic while the other system divides gels into hydrogels and organogels. Table III provides examples of both classification systems, including selected examples for each class (Allen, L. V., Popovich, N. G., Ansel, H. C., Disperse Systems, Chapter 14, in Ansel's Pharmaceutical Dosage Forms and Drug Delivery Systems, 8 ed., Lippincott Williams & Wilkins, Baltimore, Md. (2005)). These example embodiments are intended to be illustrative and are not exhaustive or intended to limit the scope of the subject disclosure.

TABLE III

General Classification and Description of Gels

| CLASS | DESCRIPTION |
|---|---|
| Inorganic | Usually two-phase systems (e.g., Aluminum hydroxide gel, Bentonite magma) |
| Organic | Usually a single-phase system (e.g., Carbomers, Tragacanth) |
| Hydrogels | Organic hydrogels (e.g., Pectin paste, Tragacanth jelly) Natural and synthetic gums (e.g., Methylcellulose, sodium carboxymethyl cellulose, Poloxamer) |

TABLE III-continued

General Classification and Description of Gels

| CLASS | DESCRIPTION |
|---|---|
| | Inorganic hydrogels (e.g., Bentonite gel, Veegum, silica) |
| Organogels | Hydrocarbon type (e.g., Petrolatum, mineral oil/polyethylene gel (Plastibase)) Animal/vegetable fats (e.g., Lard, cocoa butter) Soap base greases (e.g.. Aluminum stearate with heavy mineral oil gel) Hydrophilic organogels (e.g., Carbowax bases (PEG Ointment)) |

A fundamental concept underlying the use of a topical delivery system for drugs which exhibit significant systemic toxicity, e.g., NSAIDs, is that the drug will be rapidly transported via percutaneous absorption beneath the site of application and produce a significantly higher local tissue concentration than will be obtained with oral administration. In addition, the systemic drug concentrations attained following the topical application of an API will be significantly lower (typically about 5% or less) than those observed following an oral therapeutic dose of the drug. The difference in systemic drug levels following topical dosing will result in a reduction in adverse events compared to those seen with oral dosing. This concept has been referred to as local enhanced topical delivery (LETD) (McNeill, S. C., Potts, R. O., Francoeur, M. L. Local enhanced topical delivery (LETD) of drugs: does it truly exist? Pharm. Res. 9: 1422-1427 (1992)). The LETD concept postulates that "local accumulation of drug in target tissues occurs by direct diffusion to a greater degree than could have resulted by prior absorption and redistribution through the cutaneous vasculature" (Grahame, R. Transdermal non-steroidal anti-inflammatory agents, Brit. J. Clin. Pract. 49: 33-35 (1995)). LETD has been documented for a number of topically applied drugs by several research groups (Singh, P., Roberts, M. S., Skin permeability and local tissue concentrations of nonsteroidal anti-inflammatory drugs after topical application, J. Pharmacol. Exp. Ther. 268: 144-151 (1994); Ballerini, R., Casini, A., Chinol, M., Mannucci, C., Giaccai, L., Salvi, M., Study on the absorption of ketoprofen topically administered in man: comparison between tissue and plasma levels, Int. J. Clin. Pharm. Res. VI: 69-72 (1986); Flouvat, B., Roux, A., Delhotel-Landes, B., Pharmacokinetics of ketoprofen in man after repeated percutaneous administration, Arzneim. Forsch. 39: 812-815 (1989); Hadgraft, J., du Plessis, J., Goosen, C., The selection of non-steroidal anti-inflammatory agents for dermal delivery. Int. J. Pharmaceut. 207: 31-37 (2000); Cordero, J. A., Alarcon, L., Escribano, E., Obach, R., Domenech, J., A comparative study of the transdermal penetration of a series of nonsteroidal anti-inflammatory drugs, J. Pharm. Sci. 86: 503-507 (1997)).

Topical formulations can achieve LETD in a variety of ways, such as by the use of occlusion, the addition of penetration-enhancing agents, and the use of different molecular entities than those used in equivalent oral formulations (Dreiser, R. L., Topical antirheumatic drug therapy: current practice and future trends. Eur. J. Rheumatol. Inflamm. 14: 3-8 (1994)). One mechanism whereby LETD can occur is via the formation of intracutaneous depots in the upper layers of the epidermis. Conceivably, these depots may allow a drug to largely avoid the blood capillaries present at the epidermal-dermal junction in the skin, thereby minimizing any uptake into the systemic circulation.

While not wishing to be bound by theory, it is believed that some penetration enhancers, such as diethylene glycol monoethyl ether (DEGEE), promote the formation of intracutaneous depots of API and thereby can achieve LETD. Penetration enhancers that can promote depot formation are ideally suited for topical therapies since they increase the concentration of the drug locally, i.e., at the site of application, but inhibit the drug from being absorbed into the systemic circulation. One example compound which exhibits this property is the cosolvent DEGEE (distributed under the trademark Transcutol®P).

Table IV (Anon, Types of Topical Agents, www.Drugs.com provides a listing of several drug classes with examples of API in each class which are currently found in commercially available topical products. The exemplary API for each drug class are meant to be representative rather than exhaustive. A wide variety of API, including many of the API listed in Table IV, or other API, may be delivered topically using the methods and compositions described herein.

TABLE IV

Types of Topical Agents

| | Drug Class | Example API |
|---|---|---|
| | anorectal preparations | phenylephrine, hydrocortisone/pramoxine, pramoxine |
| | antiseptics and germicides | benzalkonium hydrochloride, chlorhexidine, triclosan |
| dermatological agents | topical acne agents | benzoyl peroxide, Evening Primrose Oil, salicylic acid, tretinoin |
| | topical anesthetics | benzocaine, lidocaine, prilocaine |
| | topical anti-infectives | crotamiton, imiquimod, ivermectin, pennethrin |
| | topical antibiotics | erythromycin, polymyxin B, sulfacetamide sodium |
| | topical antifungals | *Calendula officinalis*, ketoconazole, tolnaftate, imdecylenic acid |
| | topical antihistamines | diphenhydramine, diphenhydramine/hydrocortisone, doxepin, mepyramine |
| | topical antineoplastics | fluorouracil, imiquimod, mechlorethamine |
| | topical antipsoriatics | anthralin, calcipotriene, tazarotene |
| | topical antivirals | acyclovir, penciclovir, imiquimod |
| | topical debriding agents | balsam peru/castor oil/trypsin, bromelain, collagenase, papain/urea, |
| | topical depigmenting agents | fluocinolone/hydroquinone/tretinoin, hydroquinone, monobenzone |
| | topical emollients | ammonium lactate, urea, vitamins A, D,-and E |
| | topical keratolytics | podofilox, podophyllum resin, salicylic acid |
| | topical non-steroidal anti-inflammatories | *Arnica montana, Boswellia serrata*, bromelain, *Colchicum autmnale, Curcuma longa* (turmeric), diclofenac, ibuprofen, *Ledum palustre* (marsh-tea), quercetin, rutin, *Symphytum officinale* (comfrey), and *Zingiber officinalis* (ginger) |
| | topical photochemotherapeutics | aminolevulinic acid, 8-methoxypsoralen, trimethylpsoralen |
| | topical rubefacients | camphor/menthol, capsaicin, methyl salicylate, minoxidil, *Rhus Toxicodendron* (poison ivy), trolamine salicylate |
| | topical steroids | betamethasone, fluocinolone, triamcinolone |
| | topical steroids with anti-infectives | betamethasone/clotrimazole, fluocinolone/neomycin, nystatin/triamcinolone |
| | oral cavity preparations | chlorhexidine, minocycline, nystatin |
| | nail preparations | ciclopirox, tavaborole, Tea Tree Oil, undecylenic acid |
| nasal preparations | nasal antihistamines and decongestants | oxymetazoline, phenylephrine, tetrahydrozoline |
| | nasal steroids | fluticasone, mometasone, triamcinolone |
| ophthalmic preparations | anti-angiogenic ophthalmic agents | aflibercept, pegaptanib, ranibizumab |
| | miscellaneous ophthalmic agents | cysteamine, dapiprazole, ocriplasmin |
| | mydriatics | cyclopentolate, homatropine, tropicamide |
| | ophthalmic anesthetics | lidocaine, proparacaine, tetracaine |
| | ophthalmic anti-infectives | ganciclovir, levofloxacin, moxifloxacin |
| | ophthalmic anti-inflammatory agents | bromfenac, cyclosporine, ketorolac |
| | ophthalmic antihistamines and decongestants | naphazoline, phenylephrine, tetrahydrozoline |
| | ophthalmic diagnostic agents | fluorescein, indocyanine green, trypan blue |
| | ophthalmic glaucoma agents | latanoprost, timolol, travoprost |
| | ophthalmic steroids | dexamethasone, fluorometholone, prednisolone |
| | ophthalmic steroids with anti-infectives | dexamethasone/tobramycin, gentamicin/prednisolone, prednisolone/sulfacetamide sodium |
| | ophthalmic surgical agents | ketorolac/phenylephrine, lidocaine hydrochloride, proparacaine |
| otic preparations | cerumenolytics | carbamide peroxide, antipyrine/benzocaine/polycosanol, docusate |

TABLE IV-continued

Types of Topical Agents

| Drug Class | | Example API |
|---|---|---|
| | otic anesthetics | antyprine/benzocaine/zinc acetate, antipyrine/benzocaine, benzocaine |
| | otic anti-infectives | ciprofloxacin, m-cresyl acetate, ofloxacin |
| | otic steroids | betamethasone, fluocinolone, neomycin/polymyxin B/hydrocortisone |
| | otic steroids with anti-infectives | chloroxylenol/hydrocortisone/pramoxine, ciprofloxacin/dexamethasone, ciprofloxacinthydrocortisone |
| vaginal preparations | miscellaneous vaginal agents | amino acids/urea, conjugated estrogens, estradiol |
| | vaginal anti-infectives | metronidazole, miconazole, nystatin |

In one exemplary embodiment, the topical formulation comprises, consists essentially of, or consists of an API, a skin penetration enhancer, and a gelling agent. In some example embodiments, the API is ketoprofen, the skin penetration enhancer is a pharmaceutical grade of DEGEE, such as "Transcutol®P" as supplied by Gattefosse, and the gelling agent is a carbomer polymer, such as a Carbopol® Ultrez polymer, supplied by Lubrizol. In these and other embodiments, the formulation also includes a preservative, a chelating agent, a neutralizing agent to adjust the pH, a fragrance, and optionally, a coloring agent.

In particular embodiments where the formulation includes a preservative, the preservative may be selected from the group consisting of: ascorbyl palmitate, benzalkonium chloride, benzethonium chloride, benzyl alcohol, Bronopol, butylated hydroxyanisole (BHA), butylated hydroxytoluene (BHT), caprylyl glycol, cetrimide, chlorhexidine, chlorphenesin, dehydroacetic acid, DMDM Hydantoin, ethylhexylglycerin, Euxyl K500, Euxyl K702, Euxyl K940, Euxyl PE 9010, Germaben II, Germall Plus, glyceryl caprylate, imidazolidinyl urea, kojic acid, methylchloroisothiazolinone, methylisothiazolinone, methyl-, ethyl-, propyl-, and butylparaben, Optiphen DP, Optiphen DLP, Paragon II, Paragon III, Paragon MEPB, Paragon PPM, pentylene glycol, 2-phenoxyethanol, potassium sorbate, propyl gallate, sodium benzoate, sodium metabisulfite, α-tocopherol, tocopheryl acetate, and tropolone.

In some embodiments where the formulation includes a chelating agent, the chelating agent may be selected from the group consisting of: cyclodextrins, ethylenediamine-N,N'-disuccinic acid (EDDS), ethylenediaminetetraacetic acid (EDTA or edetate), sodium edetate, EDTA sodium, disodium EDTA, disodium EDTA dihydrate, iminodisuccinic acid (IDS), gluconic acid, L-glutamic acid N,N-diacetic acid, tetrasodium salt (GLDA), methylglycinediacetic acid (MGDA), phytic acid, polyaspartic acid, tetrasodium edetate, EDTA Tetrasodium salt, terasodium EDTA dihydrate, tetrasodium edetate tetrahydrate, or sodium phytate.

In embodiments where the formulation includes a neutralizing agent, the neutralizing agent may be selected from the group consisting of: sodium hydroxide (for example, an 18% solution); potassium hydroxide (for example, an 18% solution); ammonium hydroxide (for example, a 28% solution); L-Arginine; aminomethyl propanol (for example, AMP-95); triethanolamine (TEA) (for example, a 99% solution); tromethamine (2-Amino 2-hydroxymethyl-1, 3-propanediol) (for example, Tris Amino® (40%)); tetrahydroxypropylethylenediamine (for example, Neutrol®TE); PEG-15 Cocamine (for example, Ethomeen® C-25); diisopropanolamine; and triisopropanolamine. In some embodiments, the formulation has a pH of between 4.0 and 9.0. In select embodiments, the composition or formulation has a pH in the range of 4.4 to 5.0.

In yet another embodiment, the composition further comprises a smooth muscle relaxant, such as carisoprodol, chlorzoxazone, cyclobenzaprine, baclofen, dantrolene, metaxolone, methocarbamol, orphenadrine, or tizanidine.

In these or other embodiments, the composition further comprises an agent which can increase the blood flow to the site of administration, such as adenosine, alprostadil, amlodipine, capsaicin, diltiazem, dipyridamole, felodipine, hydralazine, isosorbide mononitrate, menthol, methyl salicylate, minoxidil, mustard oil, nicorandil, nimodipine, tartrazine, and verapamil.

In these and other embodiments, the composition further includes as the API or in addition to the API, one or more agents selected from the topical drug classes shown in Table IV or a phytomedicine including, for example, *Arnica montana, Calendula officinalis, Colchicum autumnale*, and *Rhus toxicodendron*.

As previously discussed, the topical formulations disclosed herein may include one or more ingredients, such as an API, a penetration enhancer, a gelling agent, a neutralizing agent, a chelating agent, a preservative, a fragrance, and optionally, a coloring agent. Particular examples of these ingredients are discussed below in additional detail.

Active Pharmaceutical Ingredient (API)

In some embodiments, the API of the disclosed formulations/compositions comprises drug molecules having the appropriate physical properties for effective topical delivery (Okyar, A., Özsoy, Y. and Güngör, S., Novel Formulation Approaches for Dermal and Transdermal Delivery of Non-Steroidal Anti-Inflammatory Drugs, Rheumatoid Arthritis—Treatment, Lemmey, A. (Ed.) (2012)). The "appropriate" physical properties referred to may include, a water solubility>1 mg/ml, a MW<500 Daltons, a low MP (<200° C.), and a moderate degree of lipophilicity, i.e., log P (octanol/water) of 1-3. A number of drug classes and selected examples of API in each class that are currently in use in commercial topical products are shown in Table IV. Thus, in some embodiments, the API may comprise several chemical entities useful in treating a variety of conditions where topical application is an effective mode of delivery. Numerous configurations and variations are possible upon consideration of the subject disclosure.

Skin Penetration Enhancer

As described, in some embodiments, the disclosed formulations/compositions include at least one skin penetration enhancer. In some embodiments, the penetration enhancer is present in an amount sufficient to dissolve the drug and/or to enhance skin penetration of the API. In some embodiments, the skin penetration enhancer is diethylene glycol monoethyl ether (DEGEE). Other names for DEGEE include carbitol, 2-(2-ethoxyethoxy) ethanol and ethoxydiglycol. The official United States Pharmacopeia (USP) name for this solvent is DEGEE. Cosmetic products list this ingredient as ethoxydiglycol in accordance with the International Nomenclature of Cosmetic Ingredients (INCI) Dictionary.

Pharmaceutical grade DEGEE is a transparent liquid (MW 134.2) with unique solubilizing properties. It has the ability not only to solubilize both hydrophilic and hydrophobic materials, but also has skin penetration-enhancing properties. Furthermore, it is freely miscible with polar and nonpolar solvents. It is available from Dow Chemical in two grades, cosmetic grade which is >99.0% pure and HP grade which is ≥99.5% pure. It also is marketed in a highly purified form containing >99.80% of DEGEE under the trade name Transcutol®P (Gattefossé s.a., Saint Priest, Cedex, France). It has been used as a cosolvent in topical and parenteral products (Ritschel, W. A., Panchagnula, R., Stemmer, K., Ashraf, M., Development of an intracutaneous depot for drugs. Skin Pharmacol. 4: 235-245 (1991)) and is currently used in over 500 cosmetic products (Osborne, D. W., Diethylene glycol monoethyl ether: an emerging solvent in topical dermatology products, J. Cosmetic Dermatol. 10: 324-329 (2011)).

Transcutol®P is a hydrophilic/lipophilic high purity solubilizer, with broad API compatibility that is widely used in creams, lotions and aqueous gels. It is approved for use at levels up to 49.91% w/w in topical gels by the FDA (Inactive Ingredient Search for Approved Drug Products can be found using an online drug database search provided by the U.S. Food and Drug Administration. Transcutol®P is a well-characterized, multipurpose excipient associated with interesting drug delivery properties including drug penetration enhancement and a drug depot effect. Skin penetration enhancement with Transcutol® P has been widely studied and is described as a 'push and pull' effect (Anon, Lipid excipients for topical drug delivery, Product Brochure, Gattefossé, s.a., Saint-Priest, Cedex, France) reported to increase the percutaneous transport of the API. The API must be in a solubilized state to penetrate the stratum corneum via a passive transport mechanism driven by the concentration gradient between the formulation and the skin. The solubilizing power of Transcutol®P may enable high drug loading and the generation of a steep concentration gradient down which the API is 'pushed' into the skin. Transcutol®P may induce structural deformations as it penetrates the stratum corneum. The disorganization of the intercellular space between corneocytes (composed of lipidic layers) may facilitate the diffusion of the API. This 'pull' effect has been observed for Transcutol®P in association with numerous drugs and is particularly apparent for lipophilic compounds which penetrate the stratum corneum by diffusion through these intercellular spaces.

Effective localized drug delivery relies on skin penetration and the prevention of permeation and eventual systemic absorption. Studies have shown that Transcutol® P can increase drug retention in the skin, thereby improving localized drug delivery (Ritschel, W. A. and Hussain, A. S., Influence of selected solvents on penetration of griseofulvin in rat skin, in vitro. Pharm. Ind. 50: 483-486, (1988)). In addition, the intracutaneous depot effect is associated with the swelling of intercellular lipid bilayer structures in the epidermis, which subsequently act as a depot for drug-solvent complexes, thereby enabling slow and localized diffusion of the API over time.

This phenomenon would thereby permit therapy of deep tissues beneath the site of drug administration. Such depot formation has been reported for corticosteroids (Panchagnula, R. and Ritschel, W. A., Development and evaluation of an intracutaneous depot formulation of corticosteroids using Transcutol®P as a cosolvent: in-vitro, ex-vivo and in-vivo rat studies. J. Pharm. Pharmacol. 43: 609-614 (1991)), griseofulvin (Ritschel, W. A. and Hussain, A. S., In vitro skin penetration of griseofulvin in rat and human skin from an ointment dosage form. Arzneim. Forsch./Drug Res. 38: 1630-1632 (1988)), and ivermectin (Yazdanian, M. and Chen, E., The effect of diethylene glycol monoethyl ether as a vehicle for topical delivery of ivermectin. Vet. Res. Commun. 19: 309-319 (1995)), in topical formulations containing the cosolvent Transcutol®P. Scientific studies have verified that Transcutol®P can increase significantly the flux of various compounds into and through the skin. Touitou et al (Touitou, E., Levi-Schaffer, F., Shaco-Ezra, N., Ben-Yossef, R., Fabin, B., Enhanced permeation of theophylline through the skin and its effect on fibroblast proliferation. Int. J. Pharmaceut. 70: 159-166 (1991)) were able to enhance the flux of theophylline to the dermis. Fabin and Touitou (Fabin, B., and Touitou, E., Localization of lipophilic molecules penetrating rat skin in vivo by quantitative autoradiography. Int. J. Pharmaceut. 74: 59-65 (1991)) found that Transcutol®P could improve the skin permeation of tetrahydrocannabinol and modify the location of the drug within the skin. Harrison et al (Harrison, J. E., Watkinson, A. C., Green, D. M., Hadgraft, J., Brain, K., The relative effect of Azone® and Transcutol®P on permeant diffusivity and solubility in human stratum corneum. Pharm. Res. 13: 542-546 (1996)) investigated the mechanism of the permeation enhancement of Transcutol®P and suggested that its effect was due to a change in the solubility of the permeant in the skin. Ritschel and Hussain (Ritschel, W. A. and Hussain, A. S., Influence of selected solvents on penetration of griseofulvin in rat skin, in vitro. Pharm. Ind. 50: 483-486 (1988)) concluded that Transcutol®P would be the penetration enhancer of choice if one had to deliver griseofulvin to the skin while decreasing its systemic uptake. Panchagnula and Ritschel (Panchagnula, R. and Ritschel, W. A., Development and evaluation of an intracutaneous depot formulation of corticosteroids using Transcutol®P as a cosolvent: in-vitro, ex-vivo and in-vivo rat studies. J. Pharm. Pharmacol. 43: 609-614 (1991)) reported that the permeation of dexamethasone and hydrocortisone through the skin was decreased, and penetration into the skin increased, in the presence of Transcutol®P, and concluded that intracutaneous depots of the drugs were formed. Yazdanian and Chen (Yazdanian, M. and Chen, E., The effect of diethylene glycol monoethyl ether as a vehicle for topical delivery of ivermectin. Vet. Res. Commun. 19: 309-319 (1995)) investigated the permeation of ivermectin through bovine skin and concluded that intracutaneous depots of ivermectin were formed in the presence of Transcutol®P. Panchagnula (Panchagnula, R., Development of an intracutaneous depot for drugs, Ph.D. Dissertation, University of Cincinnati (1991)) used autoradiography to demonstrate the existence of intracutaneous depots, which he proposed were formed by swelling of the intercellular lipids of the stratum corneum.

Gelling Agent

In some example embodiments, a Carbopol® polymer is used as a gelling agent in the disclosed formulations/compositions. Carbopol® polymer is a product brand name of Lubrizol Corporation. There are a number of Carbopole® polymer grades that differ greatly in their performance features. These grades are distinguished by a number designation following the brand names, e.g., Carbopol® 971P NF and Carbopol® 71G NF. The term "Carbomer" is a generic name that can be used to describe Carbopol® polymers. A carbomer is a high molecular weight polymer of acrylic acid lightly crosslinked with allyl ethers of polyalcohols. Topical preparations using various Carbopol® polymers have been available commercially for many years and their long-term safety is well established. In addition, Carbopol® polymers have a very low potential for causing skin irritation or skin sensitivity. While Carbopol® polymers have been in use for over fifty years, Carbopol® Ultrez 10 was introduced about twenty years ago in an attempt to overcome some of the shortcomings of the previous members of this series (Desai, D. D., Hasman, D. F., Schmucker-Castner, J. F., Advances in Carbomer polymer technology, BF Goodrich, Specialty Chemicals, Cleveland, Ohio 44141; Desai, D. D., Schmucker, J. F., Light, D., Carbopol® Ultrez™ 10 Polymer; a new universal thickener for the personal care industry, BF Goodrich Company, Specialty Chemicals, Cleveland, Ohio 44141). The Carbopol® Ultrez 10 polymer was developed as a culmination of research to identify a safer (benzene-free) polymerization solvent system and easy-to-disperse interpolymer carbomer technologies. It is considered a "universal" polymer, as it is capable of replacing two or more carbomer polymer grades often used to formulate lotions, creams or gels. Because of its universal rheology control characteristics (i.e., use of a single polymer instead of two or more carbomer grades) and, in some formulation scenarios, its higher efficiency compared to traditional carbomer polymers, substantial cost savings in the manufacture of personal care products may be realized with the Carbopol® Ultrez 10 polymer (Anon, Carbopol® Ultrez 10 polymer for personal care applications, TDS-225, Lubrizol Advanced Materials, Inc., Cleveland, Ohio 44141, January 2002).

Some other advantages of the Carbopol® Ultrez polymers are that the "universal" nature of the carbomer polymers (Desai, D. D., Schmucker, J. F., Light, D., Carbopol® Ultrez™ 10 Polymer; a new universal thickener for the personal care industry, BF Goodrich Company, Specialty Chemicals, Cleveland, Ohio 44141) provides the properties desired over a diverse range of product types. Such properties include clarity, highly-efficient viscosity, non-tacky feel, rich buttery texture, and ease of preservation compared to many other "natural" thickening agents. Easy dispersability of these newer carbomer polymers (the Ultrez series) speeds up the overall manufacturing process by reducing greatly the wetting time and the tendency toward clumping observed with previous carbomer polymers. The low viscosity of aqueous Carbopol® Ultrez polymer dispersions can also enable the following processing and/or cost saving advantages discussed below.

(i) Unlike the traditional carbomer polymers, it is possible to prepare very concentrated stock solutions with Carbopol® Ultrez polymers. When a master batch is needed, a single batch at a concentration as high as 5% can be made more easily and more rapidly, saving valuable production time.

(ii) If a master batch of unneutralized carbomer polymer stock dispersion needs to be pumped and transported along pipe lines within the production site, the low viscosity of Carbopol® Ultrez polymer dispersions makes this easier to accomplish.

(iii) Because of the low viscosity of concentrated Carbopol® Ultrez polymer stock dispersions, less foam is created during the initial stages of mixing due to less entrapment of air. Also, for the same reason, the subsequent mixing of additional ingredients is easy, thereby reducing the processing time. The low dispersion viscosity at high concentrations of Carbopol® Ultrez polymer dispersions is primarily due to enhanced particle behavior of the resin. Carbopol® Ultrez polymer resin thickens systems primarily because of its higher rigidity rather than its swelling behavior. In older, traditional carbomer polymer dispersions, the situation is exactly the reverse and hence the higher viscosities of their dispersions.

(iv) The unique balance between the swelling and the particle-like behavior in a Carbopol® Ultrez polymer makes it possible to create everything from thin lotions to thicker creams using only a single rheology modifier.

Until recently, the current practice in the personal care industry was to use different carbomer polymers for lotions, creams and gels depending on the desired viscosity of the final product. However, the present disclosure recognizes that individual Carbopol® Ultrez polymers can be used in products having a wide variety of viscosities. Also, the special properties of the Carbopol® Ultrez polymers result in additional performance benefits, which can include cost-efficiency and a less tacky feel. For example, the dual nature of viscosity building by the Carbopol® Ultrez polymer, i.e., thickening by swelling at concentrations (c) close to its overlap concentration $(c^*)^1$, and, thickening by its rigid particle nature at higher concentrations, leads to some interesting cost-efficiency considerations. It has been observed, for example, that certain personal care product formulations prepared with Carbopol® Ultrez polymers have 10, 20 or even 40% more viscosity than those prepared with traditional carbomer polymers, e.g., Carbopol® 934, at the same polymer concentration. Conversely, a significantly lower concentration of Carbopol® Ultrez polymer is required in a formulation to reach the same final viscosity compared to traditional carbomer polymers.

[1] The overlap concentration (c*) represents an average segment concentration of individual polymer coils. Such concentration is determined by the mass of the macromolecule and the volume that it occupies in solution.

$$c^* = M/N_A * V_M$$

where M is the molar mass of the particle, $V_M$ its volume and $N_A$ is Avogadro's number. Experimentally a marked change in behavior is observed when a certain concentration, c*, is exceeded. At c<c* the properties of individual macromolecules can be studied but at c>c* the individual macromolecules are no longer well separated from each other, and only an ensemble of many macromolecules is observed. The concentration c* is still very low ($\approx 10^{-2}$ g/ml) and the solution can certainly be considered "dilute". However, c* separates two dilute solution regimes of remarkably different behavior. To distinguish the moderately dilute solutions from the very dilute solutions the expression "semidilute" was coined to describe those that are moderately dilute. The concentration c* has a simple physical meaning. In dilute solution the coils are highly swollen, and the mean segmental concentration within a particle $c_{int}$ is rather low (<$10^{-2}$ g/ml). When the polymer concentration is increased, a stage is reached at which $c=c_{int}=c^*$. At this point the segments of the coils start to overlap and become entangled. For this reason c* is called the overlap concentration. Of course, the overall concentration can be increased beyond c* but this results in drastic changes in the solution properties (Aberle, T. and Burchard, W., Starches in Semidilute Aqueous Solution, Starch/Stärke, 49: 215-224 (1997)).

Carbopol® Ultrez polymers also swell significantly less than traditional carbomer polymers and their thixotropic index[2] is generally higher than that of traditional carbomer polymers. This unique combination of fundamental properties results in less tackiness of personal care products formulated with Carbopol Ultrez polymers compared to products thickened with older, traditional carbomers. Other easy-to-disperse interpolymer carbomer derivatives in this category, with varying physical properties and added cosmetic appeal, have been introduced i.e., Ultrez 20, 21, and 30. Improved, less tacky, feel has been observed consistently in formulations prepared in our laboratory using the Carbopol® Ultrez polymers 10, 20, 21 and 30.

[2] The Carbopol polymer systems are shear-thinning or pseudoplastic in nature, i.e., their viscosity decreases as a shear stress is applied. An example of the application of a shear stress is as simple as shaking a bottle containing the polymer. A more sophisticated way to apply a shear stress is to use a flat round plate mounted horizontally on a vertical rod (spindle). The spindle is then placed into the material to be measured and rotated at a defined speed for given time interval. This principle in used to measure viscosity in well-known devices such as the Brookfield viscometer. The Thixotropic Index is determined by measuring the viscosity of a sample at an initial (low) speed of rotation of the spindle (i.e., at a low applied shear stress) and then at a second (higher) speed of rotation (i.e., a greater applied shear stress). The second speed is typically 10 times the initial speed. A shear-thinning material will exhibit a lower viscosity as the applied shear stress (i.e., rotation speed of the spindle) is increased. Thus, for shear-thinning systems like the Carbopols the Thixotropic Index will be a numerical value greater than 1. This index therefore provides a relative measure of the material's ability to hold its shape.

These newer derivatives, i.e., Ultrez 20, 21 and 30, can be substituted for Ultrez 10 in various formulations without sacrificing the overall quality of the final formulation. All four members of the Carbopol Ultrez series have been used to successfully prepare formulations similar to those examples shown in Table V. The Carbopol® Ultrez polymer can be selected based upon the components present in the formulation and the desired properties of the final product.

Neutralizing Agent

In example formulations/compositions where a neutralizing agent is used, the neutralizing agent may be triethanolamine (TEA). Triethanolamine is supplied in a 99% pure form by Sigma Aldrich Company, St. Louis, Mo. and is one of several bases that can be used to neutralize Carbopol® polymers. Carbopol® polymers as supplied are dry, tightly coiled acidic molecules. Once dispersed in water, the molecules begin to hydrate and partially uncoil. Unneutralized dispersions have a pH range of approximately 2.5 to 3.5, depending on the polymer concentration. Unneutralized Ultrez polymer dispersions have very low viscosities. The most common way to achieve maximum thickening from Carbopol® polymers is by converting the acidic polymer to a salt. This is easily achieved by neutralizing the Carbopol® polymer with a common base such as sodium hydroxide (NaOH) or triethanolamine (TEA). In some embodiments, weaker bases, such as TEA and tromethamine, may be used rather than strong bases, such as NaOH and KOH. While either strong or weak bases may be used to adjust the pH of the formulation/composition, weak bases may be preferable where overshooting the desired pH is a concern.

Neutralization ionizes the polymer and generates negative charges along the backbone of the polymer (Anon, Neutralizing Carbopol® and Pemulen Polymers in Aqueous and Hydroalcoholic Systems, TDS-237, Lubrizol Advanced Materials, Inc., Cleveland, Ohio 44141, Sep. 16, 2009). Repulsions of like charges then cause uncoiling of the molecule into an extended structure. This reaction is rapid and gives instantaneous thickening and emulsion formation/stabilization. Optimum neutralization is achieved at a pH of 6.5-7.0, but is not necessary as sufficiently high viscosities can be achieved over a pH range of 4.5-9.0. Partial neutralization at the lower (acidic) end of this pH range permits the dispersion to achieve sufficient viscosity and yield value to gain homogeneity and the suspension of aggregate particles in a continuous phase. This creates a space-filled homogeneous dispersion that doesn't allow phase separation.

The newest member of this series, Ultrez 30, introduced on Apr. 1, 2013, has the ability to maintain a substantial viscosity-increasing effect at pH values from as low as 4 up to 12 (Moran, B., Next-generation Carbopol® polymer proves highly efficient at lower pH levels, Cosmetics and Toiletries, Vol. 128, Nov. 12, 2013). The ability to use a pH value below 5 in the disclosed formulations is advantageous for several reasons. First, the Carbopol polymers are anionic in nature and, hence, drug release from Carbopol® polymer matrices is pH-dependent. At lower pH values, the polymer is not fully swollen and there are larger regions of microviscosity. The dissolution medium can penetrate faster and deeper into the glassy core allowing the drug to be released faster, before complete gel formation occurs. As the pH increases, the ionization of the carboxylic acid groups on the polymer causes maximum swelling, resulting in fewer and smaller regions of microviscosity. The rapid gel formation acts as a barrier to the release of the drug, thus prolonging its effect. Second, for weak acid drugs such as ketoprofen (pKa 4.30) the lower pH enables a larger fraction to exist in its unionized form which has been demonstrated to penetrate the lipophilic stratum corneum barrier much more effectively than the polar ionized form of the drug (Vaidyanathan, R., Chaubal, M. G., Vasavada, R. C., Effect of pH and solubility on in vitro skin penetration of methotrexate from a 50% v/v propylene glycol-water vehicle, Int. J. Pharmaceut. 25: 85-93 (1985); Roy, S. D., Manoukian, E., Transdermal delivery of ketorolac tromethamine: permeation enhancement, device design, and pharmacokinetics in healthy humans, J. Pharm. Sci. 84: 1190-1196 (1985); Woodall, R., Arnold, J. J., McKay, D., Asbill, C. S., Effect of formulation pH on transdermal penetration of antiemetics formulated in poloxamer lecithin organogel, Int. J. Pharm. Compounding 17: 247-253 (2013)). Additionally, the lower pH is compatible with the Acid Mantle of the skin, thus enabling it to maintain its function as a protective barrier and thereby reducing the possibility of skin irritation.

Chelating Agent

In embodiments where the disclosed formulation/composition includes a chelating agent, disodium ethylenediaminetetraacetic acid (EDTA) dihydrate may be used. This salt form of EDTA is used to chelate (bind) any ions that may be present. Excessive amounts of ions present in the formulation can destabilize the Carbopol® polymer and possibly result in a loss in viscosity sufficient to render the gel unusable. Since, in some embodiments, water constitutes a major component of the formulation, deionized water should be used to minimize the impact of any ions on the stability of the formulation. In addition, the chelation of ions has been shown to inhibit the growth of certain microorganisms, thereby facilitating preservation of the formulation.

Preservative

In example formulations/compositions that include a preservative, an antibacterial agent, such as Paragon III, may be used. Preservatives may be used in cases where it is advantageous to ensure long-term stability of the formulation (and to ensure a shelf-life of ≥2 years). Paragon III (Solvay USA, Cranbury, N.J. 08152) is a broad spectrum antibacterial which also protects against mold growth and may be used in some embodiments of the disclosed formulations and compositions.

Fragrance

In some example embodiments, the formulations or compositions may include a fragrance. Fragrance may be used even in cases when the formulation has no undesirable odor, if desired. In some such embodiments, a small amount of a suitable fragrance can be added to help ensure a pleasant sensory experience. In some embodiments, the fragrance African Rain (Wellington Fragrance Company, Livonia Mich. 48150) and/or Lavender Oil (Ruger Chemical Co., Linden, N.J. 07036) may be used to enhance the aesthetic appeal of the formulation or composition.

Some examples of compositions that have been prepared and tested for sensory properties as well as clinical efficacy in treating musculoskeletal pain are provided in Table V. These examples are given in order to provide an enabling description of how to make and use the described subject matter and are not intended to limit the scope of the present disclosure.

experienced excellent pain relief and did not report any undesirable systemic side effects nor any noticeable tissue damage, irritation, or skin sensitization.

TABLE V

Examples of Four Compositions (A, B, C, D) with Carbopol Ultrez Polymers

| Ingredients | Composition A (% w/w) | Composition B (% w/w) | Composition C (% w/w) | Composition D (% w/w) |
|---|---|---|---|---|
| Ketoprofen, USP | 2.5 | 2.5 | 2.5 | 2.5 |
| Transeutol ®P | 6.7 | 5.0 | 5.0 | 5.5 |
| Ultrez 10 | 1.0 | — | — | — |
| Ultrez 20 | — | 1.1 | — | — |
| Ultrez 21 | — | — | 0.9 | — |
| Ultrez 30 | — | — | — | 1.0 |
| Triethanolamine (99%) | 0.36 | 0.34 | 0.28 | 0.36 |
| Disodium EDTA Dihydrate | 0.05 | 0.06 | 0.06 | 0.06 |
| Paragon III | 0.6 | 0.6 | 0.6 | 0.65 |
| Fragrance | 0.43 | 0.5 | 0.5 | 0.51 |
| Deionized water | 87.56 | 89.9 | 90.2 | 89.42 |
| Apparent pH | 4.9 | 5.0 | 5.1 | 4.8 |
| % Yield for 1 kg batch | 96.4% | 97.0% | 98.1% | 97.5% |

Example Method

A detailed example method of producing a 1 Kg batch formulation/composition in accordance with an embodiment of the present disclosure is provided herein for exemplary purposes.

Carbopol Ultrez polymer is dispersed stepwise in ~80% (~800 gm) of deionized water in a 1000 ml beaker with gentle stirring. EDTA is also dissolved. The water may be heated to a maximum of 50-55° C. to speed the dispersal of the Ultrez polymer. Heating may be concluded when dispersion of the Ultrez polymer is complete.

When the Ultrez polymer has fully dissolved, it may be poured it into a large stainless steel mixing bowl. If desired, the stainless steel bowl may be locked into position on a KitchenAid or other suitable mixer. The remaining weight of water may be used to rinse any residue in the Ultrez-containing beaker into the mixing bowl. The mixture may then be allowed to cool to less than 40° C.

The ketoprofen may then be dissolved in the Transcutol®P at room temperature and then added to the mixture in small portions, while being stirred. Paragon III may then be added in small portions while the mixture is stirred. If desired, fragrance may then be added dropwise to the gel and stirred.

The mixture may then be neutralized with a Triethanolamine solution, by dropwise addition until a pH of between 4.4 and 5.0 is achieved. The mixture may then be stirred until a homogenous gel forms. The pH may be estimated using short-range pH papers, then verified using a pH meter. The completed formulation may then be packaged in an opaque container, such as a tube or jar.

The treatment of musculoskeletal pain entails delivery of the active ingredient(s) (API) by applying a gel composition to the skin over the desired site of action (e.g., a painful area) by inunction for a sufficient period of time to provide the desired local effect. Example compositions in accordance with the subject disclosure have been found to be aesthetically pleasing and to provide rapid relief of musculoskeletal pain. Sample compositions in which the API was ketoprofen were used repeatedly by various subjects to treat a variety of musculoskeletal aches and pains. In all cases the subjects The compositions described herein may be used for the topical delivery of a variety of API, either alone or in combination, including both hydrophilic and hydrophobic moieties. Pharmaceutically acceptable salts, esters, amides, prodrugs, and other derivatives of the API may be used in the disclosed compositions, provided the API is pharmacologically suitable. For API that are chiral in nature, the drug may be incorporated into the composition either as the racemate or an enantiopure form. Compositions in accordance with the present disclosure may have numerous unique features and advantages, including but not limited to:

Blending into the skin quickly and providing a rapid onset of effect as a result of the enhancement of the skin penetration of the API The penetration enhancer/cosolvent used (for example, DEGEE) does not evaporate rapidly on the skin or in the container The therapeutic effect of the composition can be extended due to the formation of intracutaneous depots containing the API in the subcutaneous tissues of the skin as a result of the action of the DEGEE, preferably Transcutol®P The disclosed penetration enhancer (DEGEE) is able to dissolve a wide variety of nonpolar and hence poorly water-soluble drugs, thus maintaining the miscibility of the API solution when mixed with the aqueous gel components The unique properties of the ingredients in the disclosed compositions greatly simplify the method of manufacture compared to, for example, an emulsion whose manufacture is much more technically demanding and labor intensive The use of an aqueous solvent can improve the stability and efficacy of the API, especially compared to oil-phase API emulsions, where the low solubility of many API in the oil phase can lead to precipitation of the API during storage, thereby reducing efficacy and shortening shelf life.

The disclosed techniques and compositions provide drug delivery platforms that can be applied to the preparation of topical formulations for a variety of poorly water-soluble (and water-soluble) drugs, including: analgesics, antibacterials, antibiotics, antifungals, antihistamines, anti-inflammatory agents, anti-pruritics, antivirals, cytostatics, local anesthetics, phytomedicines, retinoids, and steroids, including the example API listed in Table IV.

The presence of the relatively non-volatile DEGEE, such as Transcutol®P (BP 196° C.), may permit the more-volatile alcoholic cosolvent components, typically ethanol (BP 78.4° C.) or isopropanol (BP 82.5° C.), present in many commonly used topical preparations, to be eliminated. The removal of volatile cosolvent components can prevent the gel from drying out in its container or on the skin too rapidly, such that a precipitate of some of the least soluble ingredients (e.g., the API) is avoided. The addition of DEGEE may also permit the preparation of a non-greasy, non-staining gel that is devoid of any unpleasant odor. Any perceived odor can be easily masked by the addition of a small amount of fragrance. Additionally, the presence of DEGEE may enhance the penetration of the API through the stratum corneum (barrier) layer of the skin into the subcutaneous tissues where the formation of intracutaneous depots of active ingredient can occur, resulting in LETD. This may provide a rapid onset and a prolonged duration of the therapeutic effect.

In the exemplary formulations shown in Table V, the model drug ketoprofen was proven to be chemically stable in the formulation for over 210 days at elevated temperature (40° C.), which indicates that a 2 year shelf-life at room temperature (23° C.) is attainable. The disclosed (gel) formulations and compositions are physically stable and exhibit no phase separation, syneresis, or significant drying out when used by patients.

Many topical gels containing carbomer polymers are neutralized to a final pH of 6.5-7.0 to "achieve a maximum viscosity". If one examines carefully the pH vs. viscosity profiles of the newer carbomer polymers used here (Anon, Neutralizing Carbopol® and Pemulen Polymers in Aqueous and Hydroalcoholic Systems, TDS-237, Lubrizol Advanced Materials, Inc., Cleveland, Ohio 44141, Sep. 16, 2009) it is evident that a viscosity at or near the maximum is maintained from about pH 4.5 to 9, or from pH 4 to 12 in the case of Ultrez 30 (Moran, B., Next-generation Carbopol® polymer proves highly efficient at lower pH levels, Cosmetics and Toiletries, Vol. 128, Nov. 12, 2013). The presently disclosed formulations may have any desired pH, including a pH within the range of 4.4 to 5.0 (where viscosity is still sufficiently high). In the example formulations using ketoprofen, the fraction of ketoprofen in its unionized form was maximized, as would also be true for other weak acid drugs. The unionized (non-polar) form of the drug is better able to partition out of the aqueous (polar) gel vehicle into and through the relatively non-polar stratum corneum more readily than the ionized form (Vaidyanathan, R., Chaubal, M. G., Vasavada, R. C., Effect of pH and solubility on in vitro skin penetration of methotrexate from a 50% v/v propylene glycol-water vehicle, Int. J. Pharmaceut. 25: 85-93 (1985); Roy, S. D., Manoukian, E., Transdermal delivery of ketorolac tromethamine: permeation enhancement, device design, and pharmacokinetics in healthy humans, J. Pharm. Sci. 84: 1190-1196 (1985); Woodall, R., Arnold, J. J., McKay, D., Asbill, C. S., Effect of formulation pH on transdermal penetration of antiemetics formulated in poloxamer lecithin organogel, Int. J. Pharm. Compounding 17: 247-253 (2013)).

The use of a pH between 4.4 and 5.0 is more closely aligned with the Acid Mantle pH of the skin, which averages about 4.7 (Wiechers, J. W., Formulating at pH 4-5: How lower pH benefits the skin and formulations, Cosmetics and Toiletries, Vol. 123 (12), pp. 61-70 (December 2008); Lambers, H., Piessens, S., Bloem, A., Pronk, H., Finkel, P., Natural skin surface pH is on average below 5, which is beneficial for its resident flora, Int. J. Cosmet. Sci. 28: 359-370 (2006)) but can range from 4.0 to 4.9 (Schmid-Wendtner, M-.H., Korting, H. C., The pH of the skin surface and its impact on barrier function, Skin Pharmacol. Physiol. 19: 296-302 (2006)), depending upon skin chemistry, body site, age, gender, race, and possibly circadian rhythm and is thus less likely to cause disruption of the protective barrier afforded by the Acid Mantle secretions. The Acid Mantle is a very fine, slightly acidic film on the surface of human skin that is secreted by sebaceous glands (Schmid-Wendtner, M-.H., Korting, H. C., Skin pH and cutaneous microflora, Chapter 5, pp. 31-43, in pH and Skin Care. ABW Wissenschaftsverlag, Berlin 10707, Germany (2007); Zlotogorski A., Distribution of skin surface pH on the forehead and cheek of adults, Arch. Dermatol. Res. 279: 398-401 (1987)), which acts as a barrier to bacteria, viruses and other potential contaminants that might penetrate the skin (Schmid M-.H., Korting H. C., The concept of the acid mantle of the skin: its relevance for the choice of skin cleansers. Dermatology (Basel). 191: 276-280 (1995)). In addition, it is important to maintain a pH below 6 since microbial growth is optimal between pH 6-8 (Elder, D. P., Crowley, P. J., Antimicrobial preservatives, Part Two: Choosing a preservative, Amer. Pharmaceutical Review, Vol. 20 (6), pp. 74-84, (September/October 2017)) thereby making preservation of the disclosed compositions (pH 4.4 to 5.0) easier to attain. Such bacterial contamination could cause a loss of skin integrity and a concomitant increase in a variety of skin disorders such as eczema, psoriasis and irritant contact dermatitis flare. The Acid Mantle pH also helps to maintain the integrity of the stratum corneum barrier since many skin enzymes important for maintaining stratum corneum lipid homeostasis have pH optima within this pH range (Ng, K. W., Lau, W. M., Skin Deep: The Basics of Human Skin Structure and Drug Penetration, In: Dragicevic, N., Maibach, H. I. (eds.) Percutaneous Penetration Enhancers-Chemical Methods in Penetration Enhancement: Drug Manipulation Strategies and Vehicle Effects. Springer, Berlin, Heidelberg, pp. 3-11 (2015)). It has recently been demonstrated that skin with pH values below 5.0 is in better condition than skin with pH values above 5.0, as shown by measuring the biophysical parameters of barrier function, moisturization, and scaling (Lambers, H., Piessens, S., Bloem, A., Pronk, H., Finkel, P., Natural skin surface pH is on average below 5, which is beneficial for its resident flora, Int. J. Cosmet. Sci. 28: 359-370 (2006)).

The presently disclosed compositions may also have other features and advantages as compared with other topical formulations, including: (1) the compositions are safe and effective; (2) the compositions use a relatively small number of commonly used and safe components and are easy to manufacture; (3) the compositions provide a consistently high yield of finished product, typically >95% for 1 Kg batches; (4) the compositions are relatively inexpensive to manufacture; (5) the compositions can be applied for an extended period, e.g., 12-15 days, without any significant risk of harmful effects; (6) the compositions are pharmaceutically elegant, i.e., aesthetically pleasing to the touch, have no runny consistency or greasy feel, and have no undesirable odor, (7) the compositions are easily removed from skin or clothing by washing with water; (8) the compositions do not stain clothing; (9) the compositions do not cause irritation, dryness, or other undesirable changes to the skin; (10) the compositions are more physically stable than an emulsion and eliminate the possibility of any creaming or cracking (i.e., phase separation) that can occur with emulsions; (11) the compositions obviate the need for a surfactant which is usually required when preparing an emulsion formulation (this is advantageous as surfactants often cause skin irritation, especially on broken skin surfaces); (12) the lower blood levels of API (e.g., an NSAID) following topical application of the presently disclosed compositions compared to those observed following oral dosing (typically 5% or less) result in a relatively low potential for the patient to experience the toxicities that can be observed following oral dosing; (13) the compositions allow the API contained therein to avoid significant metabolism in the gut or by the liver (the "first-pass" effect) because the drug does not pass through the gut or the liver before exerting its therapeutic effect; and (14) the low blood levels of API following topical application of the disclosed compositions result in a relatively low potential for drug interactions with other therapeutic agents being used by the patient.

Although example compositions and formulations have been described herein, various changes may be made to the foregoing disclosed subject matter without departing from its spirit and scope. As such, it will be apparent that other embodiments and examples may achieve like results and thus fall within the coverage and scope of the following claims. As will be understood, various adjustments and changes may be made to the foregoing disclosure without departing from the spirit and scope thereof.

What is claimed is:

1. A composition for topical application onto a mammalian body surface, the composition comprising:
    a penetration enhancer consisting of diethylene glycol monoethyl ether (DEGEE) wherein the penetration enhancer is present in a weight percent amount of between 0.10 and 49.9 of said composition;
    a gelling agent selected from the group consisting of an inorganic gelling agent, an organic gelling agent, and an organogel wherein the gelling agent is present in a weight percent amount of between 0.15 and 5.0 of said composition, and wherein the gelling agent comprises a carbomer polymer;
    an aqueous carrier; and
    at least one active pharmaceutical ingredient (API) present in a weight percent amount of between 0.01 and 50 of said composition, wherein the API comprises an active ingredient other than ketoprofen selected from the group consisting of
    (a) an anesthetic selected from the group consisting of benzocaine, lidocaine and prilocaine;
    (b) an anti-infective selected from the group consisting of crotamiton, imiquimod, ivermectin, and permethrin;
    (c) an antibiotic selected from the group consisting of erythromycin, polymyxin B, and sulfacetamide sodium;
    (d) an antifungal selected from the group consisting of *Calendula officinalis*, ketoconazole, undecylenic acid, and tolnaftate;
    (e) an antihistamine selected from the group consisting of diphenhydramine, diphenhydramine/hydrocortisone, doxepin, and mepyramine;
    (f) an antineoplastic selected from the group consisting of fluorouracil, imiquimod, and mechlorethamine;
    (g) an antipsoriatic selected from the group consisting of anthralin, calcipotriene, and tazarotene;
    (h) an antiviral selected from the group consisting of acyclovir, imiquimod and penciclovir;
    (i) a debriding agent selected from the group consisting of balsam peru/castor oil/trypsin, collagenase, papain/urea, and bromelain;
    (j) a depigmenting agent selected from the group consisting of fluocinolone/hydroquinone/tretinoin, hydroquinone, and monobenzone;
    (k) an emollient selected from the group consisting of ammonium lactate, urea, vitamin A, vitamin D, and vitamin E;
    (l) a keratolytic selected from the group consisting of podofilox, podophyllum resin and salicylic acid;
    (m) a non-steroidal anti-inflammatory drug (NSAID) selected from the group consisting of *Arnica montana, Boswellia serrata*, bromelain, *Colchicum autumnale, Curcuma longa* (turmeric), diclofenac, ibuprofen, *Ledum palustre* (marsh-tea), quercetin, rutin, *Symphytum officinale* (comfrey), and *Zingiber officinalis* (ginger);
    (n) a photochemotherapeutic selected from the group consisting of aminolevulinic acid, 8-methoxypsoralen, and trimethylpsoralen;
    (o) a rubefacient selected from the group consisting of camphor/menthol, capsaicin, methyl salicylate, minoxidil, *Rhus toxicodendron* (poison ivy), and trolamine salicylate;
    (p) a steroid selected from the group consisting of betamethasone, fluocinolone, and triamcinolone; and
    (q) a steroid/anti-infective combination selected from the group consisting of betamethasone/clotrimazole, fluocinolone/neomycin, and nystatin/triamcinolone.

2. The composition of claim 1, further comprising at least one of a preservative, a chelating agent, a neutralizing agent, a fragrance, and optionally, a coloring agent.

3. The composition of claim 2, wherein said preservative is selected from the group consisting of: ascorbyl palmitate, benzalkonium chloride, benzethonium chloride, benzyl alcohol, Bronopol, butylated hydroxyanisole (BHA), butylated hydroxytoluene (BHT), caprylyl glycol, cetrimide, chlorhexidine, chlorphenesin, dehydroacetic acid, DMDM Hydantoin, ethylhexylglycerin, Euxyl K500, Euxyl K940, Euxyl PE 9010, Germaben II, Germall Plus, glyceryl caprylate, imidazolidinyl urea, kojic acid, methylchloroisothiazolinone, methylisothiazolinone, methyl-, ethyl-, propyl-, and butyl-paraben, Optiphen DP, Optiphen DLP, Paragon II, Paragon III, Paragon MEPB, Paragon PPM, pentylene glycol, 2-phenoxyethanol, potassium sorbate, propyl gallate, sodium benzoate, sodium metabisulfite, α-tocopherol, and tocopheryl acetate.

4. The composition of claim 2, wherein said chelating agent comprises disodium ethylenediaminetetraacetic acid (EDTA) dihydrate.

5. The composition of claim 2, wherein said neutralizing agent is selected from the group consisting of: sodium hydroxide, potassium hydroxide, ammonium hydroxide, L-Arginine, aminomethyl propanol, triethanolamine, tromethamine, tetrahydroxypropylethylenediamine, PEG-15 Cocamine, diisopropanolamine, and triisopropanolamine.

6. The composition of claim 2, wherein the API is present in a weight percent amount of between 0.1 and 25.0 of said composition, the penetration enhancer is present in a weight percent amount of between 3.0 and 30 of said composition, and the gelling agent is present in a weight percent amount of between 0.3 and 3.5 of said composition.

7. The composition of claim 2, wherein the neutralizing agent is present in a weight percent amount of between 0.2 and 2.5 of said composition, the chelating agent is present in a weight percent amount of between 0.04 and 0.10 of said composition, the preservative is present in a weight percent amount of between 0.01 and 1.5 of said composition, and the fragrance is present in a weight percent amount of between 0.1 and 0.8 of said composition.

8. The composition of claim 7, wherein the neutralizing agent comprises triethanolamine and the chelating agent comprises disodium EDTA dihydrate, and has a pH between 4.0 and 9.0.

9. A composition for topical application onto g mammalian body surface, excluding the skin, the composition comprising:
　a penetration enhancer consisting of diethylene glycol monoethyl ether (DEGEE), wherein the penetration enhancer is present in a weight percent amount of between 0.10 and 49.9 of said composition;
　a gelling agent selected from the group consisting of an inorganic gelling agent, an organic gelling agent, and an organogel wherein the gelling agent is present in a weight percent amount of between 0.15 and 5.0 of said composition, wherein the gelling agent comprises a carbomer polymer;
　an aqueous carrier; and
　at least one active pharmaceutical ingredient (API) present in a weight percent amount of between 0.01 and 50 of said composition, wherein the API comprises an active ingredient other than ketoprofen selected from the group consisting of
　(a) an anorectal agent selected from the group consisting of phenylephrine, pramoxine, and hydrocortisone/pramoxine;
　(b) an antiseptic or germicide agent selected from the group consisting of benzalkonium hydrochloride, chlorhexidine, and triclosan;
　(c) an oral cavity agent selected from the group consisting of chlorhexidine, minocycline and nystatin;
　(d) a nail agent selected from the group consisting of ciclopirox, tavaborole, undecylenic acid, and Tea Tree Oil;
　(e) a nasal agent selected from the group consisting of oxymetazoline, phenylephrine, tetrahydrozoline, fluticasone, mometasone, and triamcinolone;
　(f) an ophthalmic agent selected from the group consisting of aflibercept, pegaptanib, ranibizumab, cysteamine, dapiprazole, ocriplasmin, cyclopentolate, homatropine, tropicamide, lidocaine hydrochloride, proparacaine, tetracaine, ganciclovir, levofloxacin, moxifloxacin, bromfenac, cyclosporine, ketorolac, naphazoline, phenylephrine, tetrahydrozoline, fluorescein, indocyanine green, trypan blue, latanoprost, timolol, travoprost, dexamethasone, fluorometholone, prednisolone, dexamethasone/tobramycin, gentamicin/prednisolone, prednisolone/sulfacetamide sodium, and ketorolac/phenylephrine;
　(g) an otic agent selected from the group consisting of carbamide/peroxide, antipyrine/benzocaine/polycosanol, docusate, antipyrine/benzocaine/zinc acetate, antipyrine/benzocaine, benzocaine, ciprofloxacin, m-cresyl acetate, ofloxacin, betamethasone, fluocinolone, neomycin/polymyxin B/hydrocortisone, chloroxylenol/hydrocortisone/pramoxine, ciprofloxacin/dexamethasone, and ciprofloxacin/hydrocortisone; and
　(h) a vaginal agent selected from the group consisting of amino acids/urea, conjugated estrogens, estradiol, metronidazole, miconazole, and nystatin.

10. The composition of claim 9, further comprising at least one of a preservative, a chelating agent, a neutralizing agent, a fragrance, and optionally, a coloring agent.

11. The composition of claim 10, wherein said preservative is selected from the group consisting of: ascorbyl palmitate, benzalkonium chloride, benzethonium chloride, benzyl alcohol, Bronopol, butylated hydroxyanisole (BHA), butylated hydroxytoluene (BHT), caprylyl glycol, cetrimide, chlorhexidine, chlorphenesin, dehydroacetic acid, DMDM Hydantoin, ethylhexylglycerin, Euxyl K500, Euxyl K940, Euxyl PE 9010, Germaben II, Germall Plus, glyceryl caprylate, imidazolidinyl urea, kojic acid, methylchloroisothiazolinone, methylisothiazolinone, methyl-, ethyl-, propyl-, and butyl-paraben, Optiphen DP, Optiphen DLP, Paragon II, Paragon III, Paragon MEPB, Paragon PPM, pentylene glycol, 2-phenoxyethanol, potassium sorbate, propyl gallate, sodium benzoate, sodium metabisulfite, α-tocopherol, and tocopheryl acetate.

12. The composition of claim 10, wherein said chelating agent comprises disodium ethylenediaminetetraacetic acid (EDTA) dihydrate.

13. The composition of claim 10, wherein said neutralizing agent is selected from the group consisting of: sodium hydroxide, potassium hydroxide, ammonium hydroxide, L-Arginine, aminomethyl propanol, triethanolamine, tromethamine, tetrahydroxypropylethylenediamine, PEG-15 Cocamine, diisopropanolamine, and triisopropanolamine.

14. The composition of claim 10, wherein the API is present in a weight percent amount of between 0.1 and 25.0 of said composition, the penetration enhancer is present in a weight percent amount of between 3.0 and 30 of the composition, and the gelling agent is present in a weight percent of amount between 0.3 and 3.5 of said composition.

15. The composition of claim 10, wherein the neutralizing agent is present in a weight percent amount of between 0.2 and 2.5 of said composition, the chelating agent is present in a weight percent amount of between 0.04 and 0.10 of said composition, the preservative is present in a weight percent amount of between 0.01 and 1.5 of said composition, and the fragrance is present in a weight percent amount of between 0.1 and 0.8 of said composition.

16. The composition of claim 15, wherein the neutralizing agent comprises triethanolamine and the chelating agent comprises disodium EDTA dihydrate, and has a pH between 4.0 and 9.0.

* * * * *